United States Patent
Banov et al.

(10) Patent No.: US 11,103,422 B2
(45) Date of Patent: Aug. 31, 2021

(54) DEVICE AND SYSTEM FOR REMOTE REGULATION AND MONITORING OF DRUG DELIVERY AND METHOD OF SAME

(71) Applicants: Jacob Banov, Atlanta, GA (US); Adam Verga, Newton, MA (US); Daniel Liubovich, Shrewsbury, MA (US); Brandon Kleber, Atlanta, GA (US)

(72) Inventors: Jacob Banov, Atlanta, GA (US); Adam Verga, Newton, MA (US); Daniel Liubovich, Shrewsbury, MA (US); Brandon Kleber, Atlanta, GA (US)

(73) Assignee: KBLV Medical, LLC, Atlanta, GA (US)

(*) Notice: Subject to any disclaimer, the term of this patent is extended or adjusted under 35 U.S.C. 154(b) by 0 days.

(21) Appl. No.: 16/897,232

(22) Filed: Jun. 9, 2020

(65) Prior Publication Data

US 2020/0383875 A1 Dec. 10, 2020

Related U.S. Application Data

(60) Provisional application No. 62/859,138, filed on Jun. 9, 2019.

(51) Int. Cl.
*G08B 1/00* (2006.01)
*A61J 7/04* (2006.01)
(Continued)

(52) U.S. Cl.
CPC ............ *A61J 7/0481* (2013.01); *G16H 20/10* (2018.01); *G16H 40/63* (2018.01); *G16H 40/67* (2018.01);
(Continued)

(58) Field of Classification Search
CPC ............................. A61J 7/0481; G16H 40/67
(Continued)

(56) References Cited

U.S. PATENT DOCUMENTS 4,830,224 A    5/1989    Brison
5,064,122 A   11/1991   Kamishita
(Continued)

FOREIGN PATENT DOCUMENTS

AU    2017248205 A1    11/2018
CA       2364009 C      2/2007
(Continued)

OTHER PUBLICATIONS

Timothy Aungst, "The Big List of Digital Health Medication List Companies", Nov. 2, 2018, [retrieved on May 26, 2020, Retrieved from the Internet <URL: https://www.pharmacytimes.com/contributor/timothy-aungst-pharmd/2018/11/the-big-list-of-digital-health-medication-list-companies>, 4 pages, United States of America.
(Continued)

*Primary Examiner* — Tai T Nguyen

(57) ABSTRACT

Aspects and embodiments of the present invention generally include a device for patient self-administration of a prescribed medication. The total quantity of doses to be contained in the device, the quantity of prescribed medication comprising each individual dose, and the dosing schedule, collectively referred to as prescription parameters, are determined and controlled solely by a health care provider (HCP) such as the patient's physician. In accordance with a prescribed dosing schedule, the device makes available for administration the precise quantity of prescribed medication constituting an individual dose. Patient access to the medication as well as patient control of the device is limited solely to the aspects of the device necessary to administer the available dose; that is, the patient has no control over the
(Continued)

prescription parameters utilized by the device; that is, the quantity of a dose, the availability of individual doses, the schedule at which the doses are made available to the patient, nor the prescribed medication itself which is contained in the device. Preferably, the device also has a monitored subassembly which detects and transmits relevant device information to a remote management system accessible to the HCP, including detected attempts to alter, access, control or otherwise tamper with the device beyond its prescribed use. Advantageously, HCPs may render sufficient oversight and control over the device and its use to mitigate the risks associated with patients self-administering potentially dangerous or abusable medication without direct, in-person supervision.

20 Claims, 17 Drawing Sheets

(51) Int. Cl.
    *G16H 20/10* (2018.01)
    *G16H 80/00* (2018.01)
    *G16H 40/63* (2018.01)
    *G16H 40/67* (2018.01)

(52) U.S. Cl.
    CPC .......... *G16H 80/00* (2018.01); *A61J 2200/70* (2013.01); *A61J 2205/00* (2013.01)

(58) Field of Classification Search
    USPC .......... 340/309.16, 539.1, 309.11, 5.52, 576, 340/573.4; 600/532, 572, 573; 700/237, 700/244; 221/156, 282
    See application file for complete search history.

(56) References Cited

U.S. PATENT DOCUMENTS

| | | | |
|---|---|---|---|
| 5,331,954 A | 7/1994 | Rex | |
| 5,437,267 A | 8/1995 | Weinstein | |
| 6,948,492 B2 | 9/2005 | Wermeling | |
| 7,100,601 B2 | 9/2006 | Bruna | |
| 7,743,923 B2 | 6/2010 | Conley | |
| 8,060,249 B2 | 11/2011 | Bear | |
| 8,552,868 B1 | 10/2013 | Ferguson | |
| 8,555,878 B2 | 10/2013 | Djupesland | |
| 8,744,620 B2 | 6/2014 | Shavelsky | |
| 8,786,272 B2 | 7/2014 | Carapelli | |
| 8,817,258 B2 | 8/2014 | Whalley | |
| 8,849,449 B2 | 9/2014 | Waugh | |
| 8,978,647 B2 | 3/2015 | Djupesland | |
| 9,173,837 B2 | 11/2015 | Hillis | |
| 9,361,780 B2 | 6/2016 | Burke | |
| 9,452,272 B2 | 9/2016 | Djupesland | |
| 9,456,959 B2 | 10/2016 | Reddy | |
| 9,468,729 B2 | 10/2016 | Sutherland | |
| 9,492,357 B2 | 11/2016 | MacVittie | |
| 9,550,031 B2 | 1/2017 | Van Sickle | |
| 9,953,140 B2 | 4/2018 | McLean | |
| 10,010,678 B2 | 7/2018 | Schildt | |
| 10,019,555 B2 | 7/2018 | Manice | |
| 10,065,788 B2 | 9/2018 | Fagen | |
| 10,071,022 B2 | 9/2018 | Park | |
| 10,176,663 B2 | 1/2019 | King | |
| 10,220,166 B2 | 3/2019 | Van Sickle | |
| 10,287,066 B2 | 5/2019 | Hatton | |
| 10,292,642 B2 | 5/2019 | Euliano | |
| 10,332,623 B2 | 6/2019 | Edwards | |
| 10,433,787 B2* | 10/2019 | Kanukurthy | G06K 9/00 |
| 10,441,194 B2 | 10/2019 | Robertson | |
| 10,441,511 B2 | 10/2019 | Hamilton | |
| 10,452,816 B2 | 10/2019 | Kidd | |
| 10,517,756 B2 | 12/2019 | Andino | |
| 10,555,874 B2 | 2/2020 | Feng | |
| 2007/0287753 A1 | 12/2007 | Charney | |
| 2010/0328099 A1 | 12/2010 | Wachman | |
| 2011/0166700 A1* | 7/2011 | Dunn | A61J 7/0076 700/237 |
| 2014/0236616 A1 | 8/2014 | Oberfest | |
| 2014/0278510 A1 | 9/2014 | McLean | |
| 2016/0074283 A1 | 7/2016 | Aggarwal | |
| 2017/0182258 A1 | 6/2017 | Michael | |
| 2017/0326034 A1* | 11/2017 | Lewis | A61J 7/0481 |
| 2018/0079586 A1 | 3/2018 | Burton | |
| 2019/0240430 A1 | 8/2019 | Jackson | |
| 2019/0348165 A1 | 11/2019 | Saint | |
| 2019/0392937 A1 | 12/2019 | Mensinger | |
| 2020/0009081 A1 | 1/2020 | Wang | |

FOREIGN PATENT DOCUMENTS

| | | |
|---|---|---|
| CA | 2976259 A1 | 8/2016 |
| CA | 2438977 C | 7/2018 |
| EP | 2037990 B1 | 6/2012 |
| EP | 2653183 B1 | 3/2015 |
| GB | 2570509 B | 1/2020 |
| WO | WO2005086852 A2 | 9/2005 |
| WO | WO2013025520 A2 | 2/2013 |

OTHER PUBLICATIONS adherium, "Proven Health Technologies", 2020, [retrieved on May 26, 2020], Retrieved from the Internet <URL: https://www.adherium.com/technology/>, 4 pages, New Zealand.

e-pill, "MedSmart", 2020, [retrieved in 2020], Retrieved from the Internet <URL: https://www.epill.com/medsmart.html>, 3 pages, United States of America.

MedVault, "About MedVault", 2020, [retrieved on 2020], Retrieved from the Internet <URL: https://medvault.wordpress.com/about/about-medvault/>, 1 page, United States of America.

aavia, "aavia", 2020, [retrieved on Jun. 6, 2020], Retrieved from the Internet <URL: https://aavia.io/>, 4 pages, United States of America.

Janssen Pharmaceuticals, Inc., "About Spravato", 2019-2020, [retrieved on 2019], Retrieved from the Internet <URL: https://www.spravato.com/what-is-spravato>, 9 pages, United States of America.

Popit, "Popit", 2020, [retrieved on Jun. 6, 2020], Retrieved from Internet <URL: https://popit.io/>, 7 pages, Finland.

AptarGroup, Inc., "E-Lockout", 2020, [retrieved on 2020], Retrieved from Internet <URL: https://pharma.aptar.com/en-us/dispensing-solutions/e-lockout.html>, 1 page, United States of America.

Pillpresso, "pillpresso", 2020, [Retrieved on Jun. 6, 2020], Retrieved from Internet <URL: https://pillpresso.com/>, 5 pages, United States of America.

Mamta Kapoor, A review of intranasal formulations for the treatment of seizure emergencies, Journal of Controlled Release, Sep. 10, 2016, 147-159, vol. 237, Elsevier B.V., USA.

Nemera, "Safe'n'Spray™: the smart electronic concept device with locking features," 2019-2020, [retrieved in 2019], Retrieved from Internet <URL: https://www.nemera.net/products/ear-nasal-throat/safenspray/>, 1 page, France.

Jon Hamilton, "FDA Approves Esketamine Nasal Spray for Hard-To-Treat Depression", 2019-2020, [retrieved in 2019], Retrieved from Internet <URL: https://www.npr.org/sections/health-shots/2019/03/05/700509903/fda-clears-esketamine-nasal-spray-for-hard-to-treat-depression>, 4 pages, United States of America.

Per Gisle Djupesland, Nasal drug delivery devices: characteristics and performance in a clinical perspective—a review, Drug Delivery and Translational Research, Oct. 18, 2012, 42-62, vol. 3(1), National Center for Biotechnology Information, U.S. National Library of Medicine, Bethesda, MD.

Ulrika Westin Espefalt, Olfactory Transfer of Analgesic Drugs After Nasal Administration, Digital Comprehensive Summaries of Uppsala Dissertations from the Faculty of Pharmacy 55, Apr. 19, 2007, Uppsala Universitet, Sweden.

Bjorn Jansson, Models for the Transfer of Drugs from the Nasal Cavity to the Central Nervous System, Comprehensive Summaries

(56) References Cited

OTHER PUBLICATIONS of Uppsala Dissertations from the Faculty of Pharmacy 305, Jan. 30, 2004, Uppsala Universitet, Sweden.

Medminder Systems, Inc., "Locked Pill Dispenser", 2019, [retrieved on Feb. 24, 2019], Retrieved from Internet <URL: https://www.medminder.com/pill-dispenser/locked-pill-dispenser/>, 5 pages, United States of America.

Degenhard Marx, Multi-Dose Container for Nasal and Ophthalmic Drugs: A Preservative Free Future?, Aptar, Dec. 7, 2011, 509-524, InTechOpen, Germany.

Limor Wainstein, "Cloud-Based Telehealth Defined: Advantages, Applications, and Security", Jun. 26, 2018, [retrieved on Feb. 24, 2019], Retrieved from internet <URL: https://telemedicine.arizona.edu/blog/cloud-based-telehealth-defined-advantages-applications-and-security>, University of Arizona Telemedicine Program, Arizona, USA.

Kiao Inthavong, Optimising nasal spray parameters for efficient drug delivery using computational fluid dynamics, Computers in Biology and Medicine, 713-726, vol. 38(6), Jun. 2008, Elsevier, Australia.

Raepak LTD, "Nasal Spray Pump—Clip Lock", 2019, [retrieved on Feb. 24, 2019], retrieved from internet <URL: https://www.raepak.com/product/nasal-spray-pump-clip-lock/>, 5 pages, United Kingdom.

Philip Chen, Sinus Penetration of a Pulsating Device Versus the Classic Squeeze Bottle in Cadavers Undergoing Sinus Surgery, Annals of Otology, Rhinology & Laryngology, 9-13 , 126(1), Sep. 29, 2016, San Antonio, Texas.

International Search Report of the International Searching Authority, for corresponding PCT Application US2020/036858, dated Oct. 15, 2020.

\* cited by examiner

DEVICE AND SYSTEM FOR REMOTE REGULATION AND MONITORING OF DRUG DELIVERY AND METHOD OF SAME

RELATED APPLICATIONS

The present application claims the benefit of U.S. Provisional Patent Application 62/859,138, filed Jun. 9, 2019.

STATEMENT REGARDING FEDERALLY SPONSORED RESEARCH OR DEVELOPMENT (Not Applicable)

BACKGROUND

Field of the Invention

The present application is directed generally toward medication administration, and in particular, to patient self-administration of a prescribed medication.

Related Art

Few technologies exist that allow for health care practitioners to have optimal oversight over patients when the patients are not in their immediate care. This lack of oversight is most evident in patient use of prescription medications. A substantial percentage of patients fail to fill their prescriptions, and a substantial percentage of those that fill their prescriptions, fail to take the medications as prescribed. And of those patients that follow the prescription, many fail to do so continuously or consistently. This is further compounded by the misuse of prescription medications, either due to abuse or error. As a result, the administration of the more acutely dangerous prescription medications as well as the administration of medications to treat a serious medical condition, typically require the medication to be administered under the immediate care of a health care practitioner.

SUMMARY

Aspects and embodiments of the present invention generally include a device for patient self-administration of a prescribed medication. The total quantity of doses to be contained in the device, the quantity of prescribed medication comprising each individual dose, and the dosing schedule, collectively referred to as prescription parameters, are determined and controlled solely by a health care provider (HCP) such as the patient's physician. In accordance with a prescribed dosing schedule, the device makes available for administration the precise quantity of prescribed medication constituting an individual dose. Patient access to the medication as well as patient control of the device is limited solely to the aspects of the device necessary to administer the available dose; that is, the patient has no control over the prescription parameters utilized by the device; that is, the quantity of a dose, the availability of individual doses, the schedule at which the doses are made available to the patient, nor the prescribed medication itself which is contained in the device. Preferably, the device also has a monitored subassembly which detects and transmits relevant device information to a remote management system accessible to the HCP, including detected attempts to alter, access, control or otherwise tamper with the device beyond its prescribed use.

Aspects and embodiments of the present invention are further directed to a system in which the functionality of the device is remotely monitored and controlled by the patient's physician or other HCP. HCP regulatory commands include, for example, commands to alter the dosing quantity and/or schedule, to permit access to the device for prescription refills, as well as to cease operability of the device should it be tampered with or reported lost or stolen. The device is further configured to send monitored parameters to, and receive control commands from, a remote server of the system on which a patient management software is executing, at least in part. This server is configured to provide the HCP with access to relevant data and controls. Some embodiments of the system further comprise a patient interface for data input, oversight and notifications.

BRIEF DESCRIPTION OF THE DRAWINGS

The features and advantages of the described aspects and embodiments of the present invention will be more clearly appreciated from the following detailed description, when taken in conjunction with the accompanying drawings. The accompanying drawings are not drawn to scale. In the drawings, each identical or nearly identical component that is illustrated in various figures is represented by a like or similar reference numeral or descriptor. For purposes of clarity, not every component may be labeled in every drawing. The drawing figures are.

DETAILED DESCRIPTION

Figure 1:
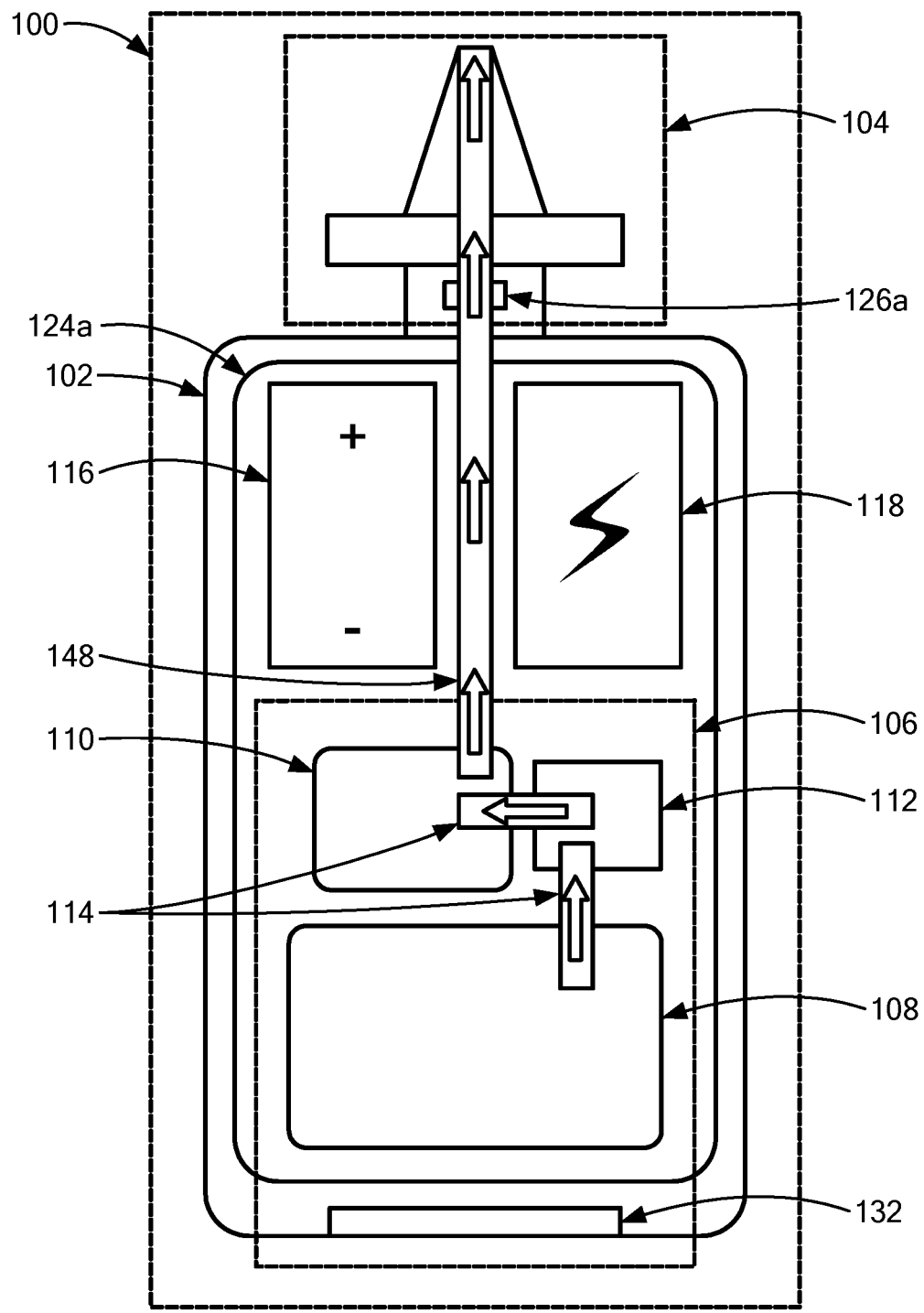
FIG. 1 is a schematic block diagram of one embodiment of a medication self-administration device.

Aspects and embodiments of the present invention generally include a device for patient self-administration of a prescribed medication. The total quantity of doses to be contained in the device, the quantity of prescribed medication comprising each individual dose, and the dosing schedule, collectively referred to as prescription parameters, are determined and controlled solely by a health care provider (HCP) such as the patient's physician. In accordance with a prescribed dosing schedule, the device makes available for administration the precise quantity of prescribed medication constituting an individual dose. Patient access to the medication as well as patient control of the device is limited solely to the aspects of the device necessary to administer the available dose; that is, the patient has no control over the prescription parameters utilized by the device; that is, the quantity of a dose, the availability of individual doses, the schedule at which the doses are made available to the patient, nor the prescribed medication itself which is contained in the device. Preferably, the device also has a monitored subassembly which detects and transmits relevant device information to a remote management system accessible to the HCP, including detected attempts to alter, access, control or otherwise tamper with the device beyond its prescribed use. Advantageously, HCPs may render sufficient oversight and control over the device and its use to mitigate the risks associated with patients to self-administering potentially dangerous or abusable medication without direct, in-person supervision.

Aspects and embodiments of the present invention are further directed to a system in which the functionality of the device is remotely monitored and controlled by the patient's physician or other HCP. HCP regulatory commands include, for example, commands to alter the dosing quantity and/or schedule, to permit access to the device for prescription refills, as well as to cease operability of the device should it be tampered with or reported lost or stolen.

The device is further configured to send monitored parameters to, and receive control commands from, a remote server of the system on which a patient management software is executing, at least in part. This server is configured to provide the HCP with access to relevant data and controls. Some embodiments of the system further comprise a patient interface for data input, oversight and notifications. Some embodiments of the system also further comprise additional external devices for any number of functions, some examples include biometric sensors, user-identifying sensors, and global positioning systems.

Other embodiments include additional features to monitor patient biometrics directly or indirectly via third-party medical equipment. In such embodiments, the device may be programmed by the HCP to alter the dosing parameters or device functionality based on the availability and specified range of such biometric values. Advantageously, such embodiments provide additional levels of security and safety, ensuring that the device is utilized by the intended people, and that the patient's daily health condition does not warrant a change or cessation of the prescription.

As noted, aspects of the present invention are directed to a device for use by a patient to self-administer a prescribed medication, generally referred to herein as a medication self-administration device. The preferred form in which a prescribed medication is to be administered depends on numerous factors, such as the bioavailability in a given form, location of the target area, and intended therapeutic effects. As such, various embodiments of the device are each configured to be used by a patient to administer a prescribed medication in the prescribed form and in accordance with the recommended method of delivery.

These delivery methods include, for example, spray for the delivery of mist, which is typically delivered to the nasal passage, atomizer for the delivery of mist or vapor, typically delivered to the nasal passages and/or the lungs, and more specifically, a nebulizer which is often used for the delivery of a mist to the lungs. Some embodiments may deliver a fluidic medication via intramuscular or intravenous injection, while other embodiments may have the medication in aerosol form for inhalation. Furthermore, larger droplets or even a stream of liquid may also be administered in certain embodiments. It should also be appreciated that as used herein, the term "self-administration" refers generally and collectively to direct and indirect administration of a prescribed medication. For example, large droplets or a liquid stream of a prescribed medication may be administered directly to the nasal passage in one embodiment of the device, or administered indirectly using the same or different embodiment of the device. An example of indirect delivery methods include but are not limited to the dispensing of droplets or a liquid stream into an external container to be titrated; that is, mixed with water, prior to being ingested by drinking. Other examples of indirect delivery methods are the spraying of a mist into an external holding chamber prior inhaling and the dispensing of solid-phase medication for ingestion or otherwise.

Aspects and embodiments of the present invention will be described in connection with an exemplary medication self-administration device, a nasal delivery device configured to deliver a prescribed fluid medication in an aerated form to a nasal cavity. It should be appreciated, however, that in alternative embodiments the medication self-administration device may be configured to deliver other forms of a prescribed medication to other target areas or indirectly, as noted above.

Figure 5A:
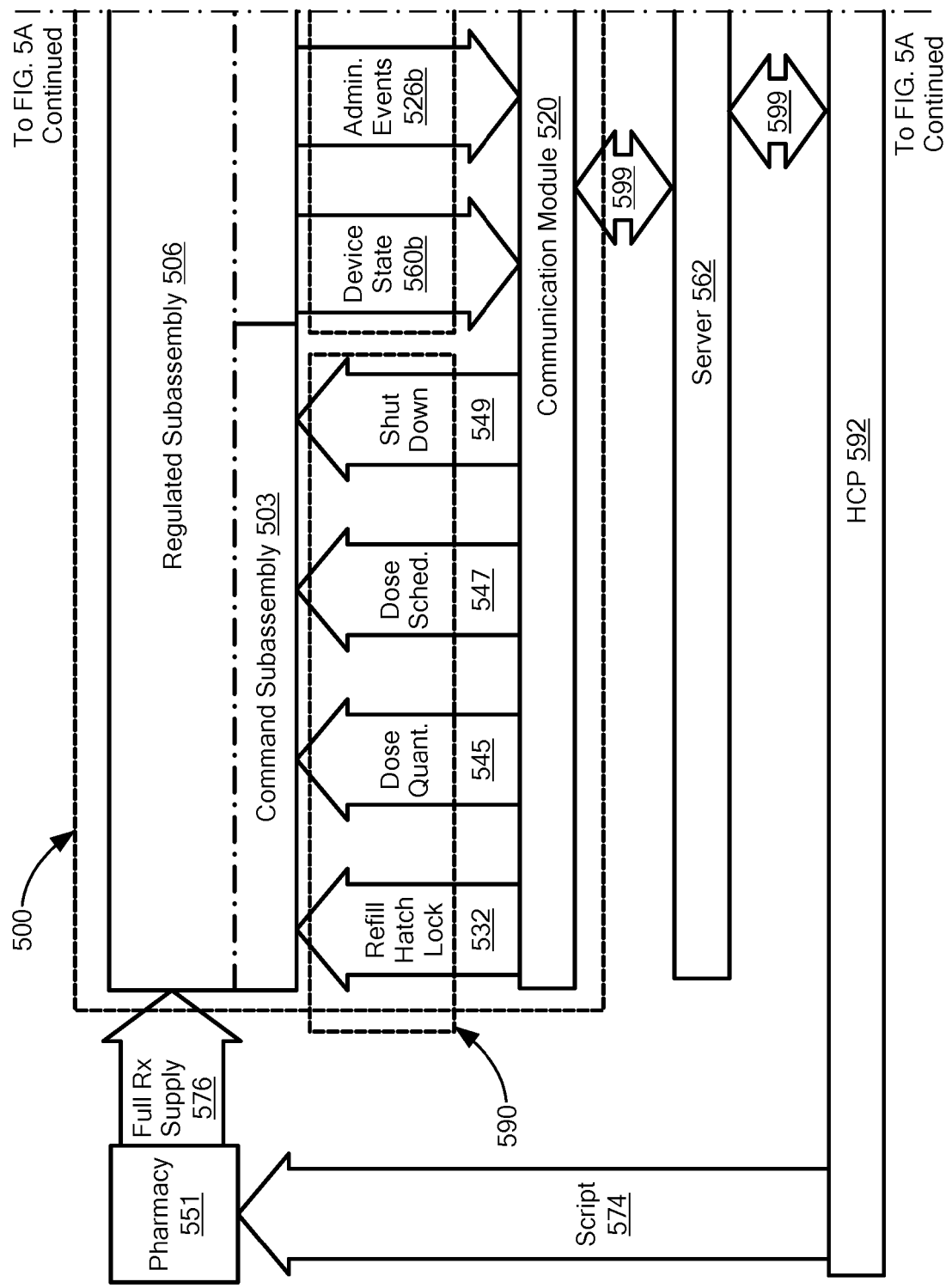
FIG. 5A is a functional block diagram of an exemplary system of the present invention.
Figure 5A:
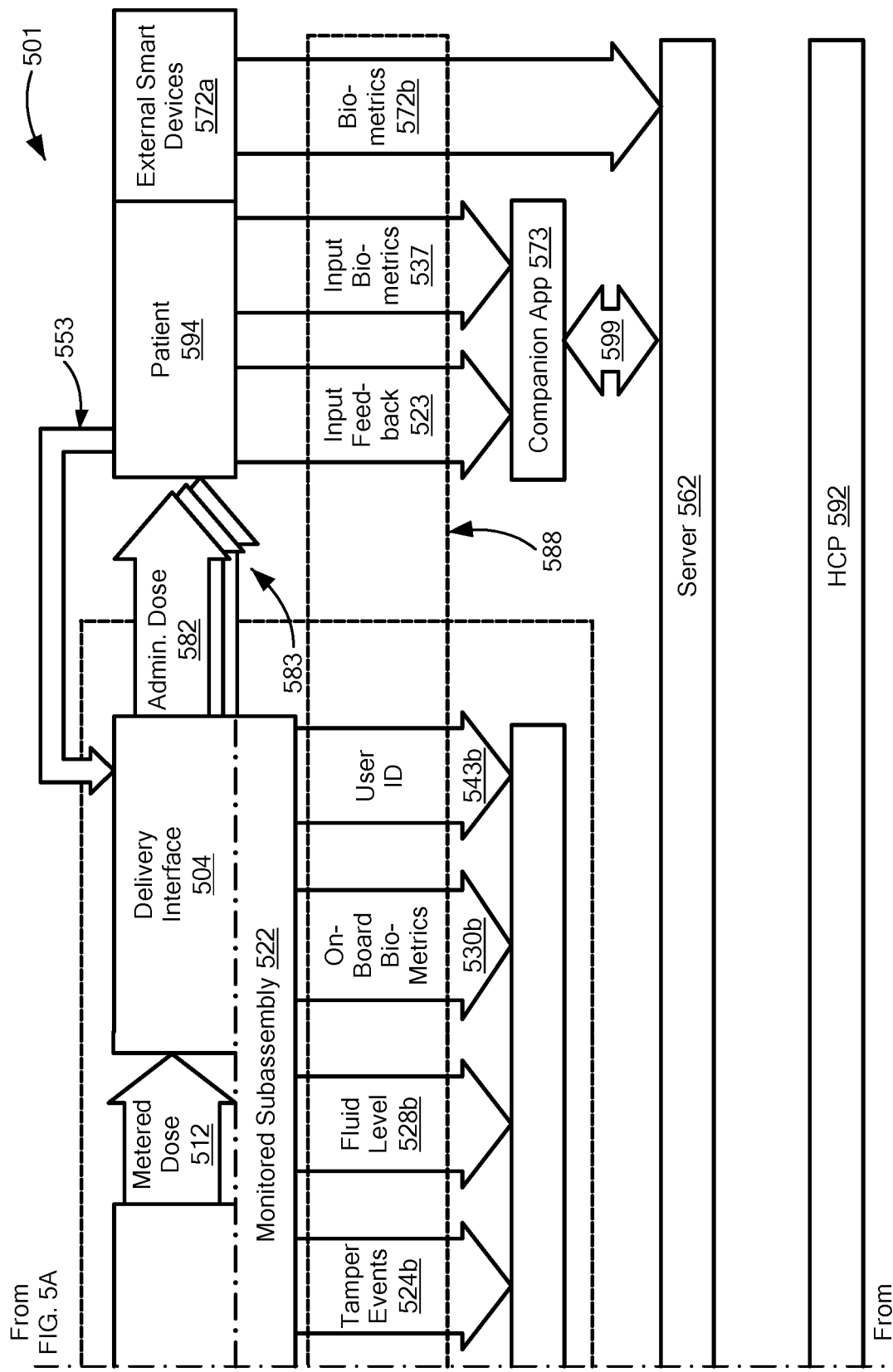

FIG. 5A is a functional block diagram of an exemplary system of the present invention. System 501 includes an exemplary medication self-administration device 500. Device 500 receives prescribed medication 576, typically from a pharmacy 551. As noted, The total number of doses contained in a medication self-administration device of the present invention is determined and controlled solely by a health care provider, shown as HCP 592 in FIG. 5A. Such a health care provider may be, for example, the patient's physician, a physician's assistant (PA), nurse practitioner (NP), and/or others that operate under the direction and supervision of the patient's physician.

HCP 592 provides a prescription 574 to pharmacy 551 specifying the requisite prescription parameters so that pharmacy 551 is able to dispense the total quantity of medication to device 500 for a patient 594. This quantity of medication, referred to herein as a full Rx supply 576 of such medication, is delivered directly into device 500 by pharmacy 551. It is anticipated that the form of the prescribed medication is likely to be a fluid. As such, prescribed medication 576 may be poured or otherwise fluidically transferred directly, or via an attached tubing, into a chamber in the device via an appropriately configured delivery port. Alternatively, pharmacy 551 may inject the prescribed medication through a silicone seal. In alternative embodiments, full Rx supply 576 may be provided in a sealed container which is physically inserted through an aperture into a compartment of device 500. Whether such access is provided by a port, injection seal, aperture or other structure or mechanism, device 500 preferably includes a secure hatch through which such port, injection seal or aperture is accessed should the device be filled by pharmacy 551 or HCP 592. In some embodiments, device 500 is filled with medication by the manufacturer before distribution, preferably the case for disposable embodiments of device 500.

Device 500 includes a regulated fluidics subassembly 506 configured to receive and securely store full Rx supply 576 of a prescribed medication, and to make available for administration the precise prescribed individual dose of the stored medication, referred to herein as metered dose 512. Regulated subassembly 506 is responsive to remotely generated control signals 590 generated by HCP 592 to manage the operation of—that is, to regulate—device 500. As such, control signals 590 are sometimes referred to herein as regulatory commands or regulatory control signals. Control signals 590 may be transmitted directly to device 500 from HCP 592, such as through a networked computer local to HCP 592 which is communicably connected to device 500, or indirectly by HCP 594, such as by invoking software executing on server 562 to generate such commands 590. The networked communications between HCP 592 and server 562, and between server 562 and device 500, are schematically depicted in FIG. 5A as arrows 599.

Remotely generated control signals 590 include, for example, the noted prescription parameters such as dose quantity 545 and dose schedule 547 (the total quantity of prescribed medication being specified or derived from prescription parameters contained in prescription 574, as noted above). Other control signals 590 include, for example, device shut-down control signal 549, which will cause device 500 to cease operation.

Command subassembly 503 of device 500 generates signals to control regulated subassembly 506 in response to regulatory commands 590 generated by HCP 592 and transmitted to device 500. The outputs of command subassembly 503 may take on any form suitable for the controlled components. For example, command subassembly 503 may generate electronic signals, may shift the voltage on certain input pins of a component, may write data to a microcontroller memory of a component, and so on. As such, for ease of description, the outputs and actions of command subassembly 503 are also referred to herein as command signals 590.

In some embodiments, as mentioned above, the restricted components of the regulated subassembly may be accessible to a party that is not the patient, for example HCP, manufacturer, distributor, etc. for reasons which may include but are not limited to refilling, refurbishing, and maintenance. In those embodiments in which device 500 is to be refilled, regulatory control commands 590 preferably include a hatch lock command 532. HCP 592 directly or indirectly generates a hatch lock command 532 to unlock such a hatch so that pharmacy 551 may access device 500 and refill the prescription. Although in FIG. 5A hatch lock command 532 is shown as being remotely generated by HCP 592, it should be appreciated that in alternative embodiments, hatch lock command 532 may be generated by pharmacy 551 or other HCP, depending on the protocols established to ensure safe administration of the prescribed medication.

As noted, in response to a prescribed dosing schedule 574, regulated subassembly 506 makes available for administration metered dose 512 which is the precise individual dose of the medication prescribed by HCP 592 in dose quantity 545. A medication delivery interface 504, responsive to patient control actions 553, retrieves, receives or otherwise accesses metered dose 512, and delivers metered dose 512 of the prescribed medication to patient 594 as administered dose 582.

As noted, aspects of the present invention are directed to a device for use by a patient to self-administer a prescribed medication. Various embodiments of device are each configured to be used to administer a prescribed medication in a prescribed form or state (liquid, gas, mist, etc.) and in accordance with the recommended or required delivery method (nasal spray, inhaler, injection, etc.) Depending on the quantity of medication contained in an individual metered dose 512, the form of the administered medication, the specified delivery method, the characteristics of the target delivery location, as well as the conditions and characteristics of patient 594, administered dose 582 may be delivered in a series of two or more applications 583 to patient 594. For example, patient 594 may be unable to tolerate, swallow, inhale or otherwise therapeutically accept a single application 582 of dose quantity 545 of medication at one time. Embodiments of device 500 employed under such circumstances preferably comprises a device interface 504 configured to enable patient 594 to control, via patient actions 553, the portion of metered dose 512 which is to be delivered in each successive application 583.

A monitored subassembly 522 comprises passive and/or active components described below to detect device operations and operational states, which may include but are not limited to data regarding measure fluid levels or quantities, detect physical shocks, device modification and disassembly attempts, fluid escape or leakage, and other device parameters. Some embodiments of the monitored subassembly may further be configured to detect patient parameters, such as biometrics and/or user identity. It should be appreciated that such measuring, sensing, detecting, etc., may be conducted by sensors located in regulated subassembly 506 and delivery interface 504 as well as other components of device 500 such as its housing, etc. Alternatively or additionally, such monitored device parameters may be retrieved from the memory in, or interpreted based on signals generated by, components included in subassembly 506 and interface 504. To reflect this flow of information, the boundaries between monitored subassembly 522 and regulated subassembly 506 and delivery interface 504 are depicted in FIG. 5A as being porous, as shown by dashed lines in the figure.

Monitored subassembly 522 is further configured to store and transmit such monitored device parameters to a remote server 562 for processing by a patient management software executing at least in part on server 562, and/or for access by/presentation to HCP 592. Such transmission may occur immediately, in accordance with a predetermined schedule or in response to a request for such data by server 562. The functions and operations performed in system 501 to transmit and process monitored device parameters are collectively and generally referred to herein as remote monitoring 588.

In the embodiment of system 501, the device parameters that are gathered by monitored subassembly 522 and transmitted to server 562 include device operational states 560b such as the current charge of an onboard rechargeable battery, the position or state of the refill hatch, if any, the position, orientation, etc., of any electromechanical components of regulated subassembly 506, the functional health of such device components, etc.

Monitored device parameters of system embodiment 501 also include fluid levels 528b of the medication contained in device 500. If such medication is distributed in regulated subassembly 506, then the fluid levels at each location of the medication is preferably monitored and included in fluid levels 528b. For device 500 embodiments configured for medication forms other than fluids, this parameter could be a measure of weight, volume, quantity, or any other metric that could indicate an amount of medication in a given location within device 500.

Administration event data 526b collected by monitored subassembly 522, in some nasal spray configurations of device 500, may be collected by one or more contact sensors located so as to detect when the nozzle has been depressed, and/or a fluid flow sensor or fluid level sensor. In other such embodiments, a sensor detects the distance the plunger travels. In some embodiments of device 500 which are intended for use with medications in forms other than a fluid, other types of sensors may be used which serve the function of detecting an administration event. Such detection methods may include but are not limited to detection of changes in mass within device 500, disruptions to an optical beam, an imaging sensor, or any other method which may serve this purpose.

In embodiments of device 500, monitored device parameters include tamper events 524b reflecting any sensed or detected event, the occurrence of which may be as a result of an attempted unauthorized use of device 500. For example, in some embodiments, device 500 includes one or more accelerometers to detect the application of forces greater than those that may occur during everyday use. Physical shocks of such magnitude indicate potential attempted breach of the device suitable for reporting to server 562 and HCP 592. Other embodiments may include a circuit network whose electrical feedback would change after physical manipulation or contact. Whether due to intentional tampering or accidental handling, such sensor(s) may be activated whenever the functionality of device 500 has possibly been compromised. This sensor could be of any nature which effectively accomplishes this task. When the device is unlocked during the refill process, tamper detection 524b may be expected and could serve as a functionality check of the tamper sensor. In other embodiments, monitored subassembly 522 includes electronic contacts to detect any adjustment of mated parts. Attempts to access the prescribed medication in device 501 by disassembling the device will be detected by such contacts and reported to server 562 and HCP 592. In other embodiments, monitored subassembly 522 includes piezoelectric sensors to measure changes in strain or force in regulated subassembly 506, processing and interpreting signals from such sensors to determine potential tampering or unauthorized access. Some other embodiments of device 500 may detect tampering with changes in internal pressures, the detection of light leakage into a region of the device normally kept dark, and the detection of oxygen or another gas or substance in a region of the device normally void of it.

Some embodiments of device 500 include a reactive agent which is released into the medication chamber(s) upon tamper event signal 524b and renders the medication harmless. Such an agent could be released automatically by software on device 500 or after receiving a command from HCP 592. In one such embodiment, this agent is released by a mechanical assembly which is activated by software automatically upon a detected tamper event. In another possible embodiment, the agent is released by an impact upon the device, such as a user bashing the device with a hammer in an attempt to access more medication than intended.

It should be appreciated that monitored subassembly 522 may include other types of sensors deemed appropriate to monitor the use and condition of device 500 and to provide such information to server 562 or HCP 592 to ensure proper administration of prescribed medication 576. For example, in some embodiments, monitored subassembly 522 includes capacitance sensors to detect leakage or other changes in the normal operating environment of device 500.

Remote monitoring 588 also contains structural and functional components for monitoring patient 594. For example, monitoring biometric data derived from or provided by patient 594 may be considered in connection with treatments involving certain prescribed medications. Specific biometric data may be considered, for example, during the course of treatment with the prescribed medication. Similarly, the condition of patient 594 may need to be considered prior to permitting device 500 to deliver each successive dose of prescribed medication. In many circumstances the condition of patient 594 that is of concern may be obtained by biometric sensors in device 500 and the resulting biometric data 530B included in remote monitoring 588. Depending on the implementation, HCP 592 may adjust the dose quantity 545 or schedule 547 based on received biometrics 530b. In such embodiments, HCP 594 review of certain biometric data may be a prerequisite to enabling regulated subassembly 506 to make a metered dose 512 available for device interface 506. It should be appreciated that in some embodiments, such a determination may be made by monitored subassembly 522, programs executing on server 562 or HCP 592. Other embodiments include additional security features to confirm patient identity so that only the intended patient (or patient's approved caregiver) may operate the device.

In the illustrative embodiment of system 501, the patient parameters that are gathered by monitored subassembly 522 and transmitted to server 562 include patient validation information such as user identification security data 543b and patient biometrics 530b measured by onboard biometric measurement devices (not shown). Monitored patient parameters further include parameters that are not directly obtained from patient 594 by device 501; rather such patient biometric data may be inferred from the noted device parameters. For example, the time at which administration event 526b indicates device 500 was used to deliver administered dose 582, and the quantity of medication included in administered dose 582, may be used to estimate the quantity of medication remaining in patient 594 at some time subsequent to the time of administration. Besides enabling HCP 592 to confirm when prescribed dose 582 has been administered, HCP 592 may determine whether to alter dose schedule 547 should the scheduled time of the next dose be too soon given the estimated or measured blood concentrations of the medication. Such information will also be used to determine the quantity of prescribed medication remaining in device 500 thereby enabling HCP 592 to determine how best to proceed with patient 594.

In some embodiments of system 501, additional features are utilized to more closely manage patient 594 as the patient uses device 500 to self-administer a prescribed medication. For example, some embodiments of system 501 are configured to receive specific biometric data 572b from a third-party device 572a. Biometrics 572b may be received directly from device 572a or via a database associated with device 572a. For those devices that are not capable of transmitting data electronically, that data, referred to as biometrics data 537, may be manually entered into a software program accessible to patient 594. Such a software program may be configured to execute on server 562 which is remotely accessible by a local computer such as a smartphone, laptop, desktop computer or other computing device.

To satisfy the patient's need for easy access to personal treatment data and a method for easily communicating information to their physician, some embodiments of system 501 further comprise a patient interface, here implemented as a companion application 573 to be accessed via the patient's smartphone or other computing device 568. Patient interface 573 may include features 586 enabling the input of data and feedback, treatment oversight tools 571, and notifications 569. Such a software 573 may be configured to enable patient 594 to provide objective (measured) or subjective biometric data and other information. The companion application user interface could allow for the manual input of data, such as feedback 523 including side effects, as well as biometric data 537, and the transmission of this data to the physician via programs executing on server 562. In that way, such programs can consolidate such information with other information related to patient 594 and device 500. Companion application 573 could also make viewable to the patient their personal treatment data, such as real-time updates and reminders, administration log, and calendar.

An example of manually input biometrics 537 is the patient's weight, derived from a standard weight scale, where the patient can be trusted to measure themselves and record their weight. In some embodiments of the system 501, some biometric sensors are internet-connected and communicate directly with the system 501 and server 562 itself, and shall be referred to as smart external biosensors 572a. One possible embodiment of a sensor 572a could be a blood pressure/heart rate monitor, a continuous or discrete blood glucose monitor, oximeter, etc. Other possible embodiments of biosensors 572a include implanted and/or ingestible biometric sensors.

As shown in FIG. 5A, device 500 comprises an electronic communication module 520 configured for transmitting and receiving information via local and global networks, as is well known in the art. Some embodiments of communication module 520 utilize wireless communications; such modes of communication include but are not limited to radio, Wi-Fi, Bluetooth, and LTE. Other embodiments of communication module 520 communicate with the internet via a wired connection. Thus, it should be appreciated that while some embodiments of communication module 520 communicate directly with the internet, for example through Wi-Fi, other embodiments communicate indirectly with the internet, for example via a Bluetooth connection between the device and a smartphone, which is itself wirelessly connected to the internet via a mobile cellular network or wi-fi connection with a local network. Exchanged information may include but is not limited to the sensor data collected by the monitored subassembly 522 and any commands intended for the command subassembly 503 (and hence the regulated subassembly 506).

It should be appreciated that device 500 may take on a myriad of configurations depending on the risk profile of the prescribed medication, and the prescribed delivery formand method. It is envisioned, therefore, that all or part of device 500 may be handheld, wall mounted, or a desktop or floor-based design.

It should also be appreciated that patient access to the medication as well as patient control 553 of device 500 is limited solely to the administration of the available dose in delivery interface 504; the patient has no control over the quantity of a dose, the availability of individual doses, the schedule at which the doses are made available to the patient, nor the prescribed medication itself stored in regulated subassembly 506. Advantageously, embodiments of system 501 and device 500 may be used by HCPs to allow patients to self-administer potentially dangerous/abusable medication without direct, real-time supervision, confident that the patient will be unable to administer the prescribed medication other than exactly as it was prescribed.

Figure 5B:
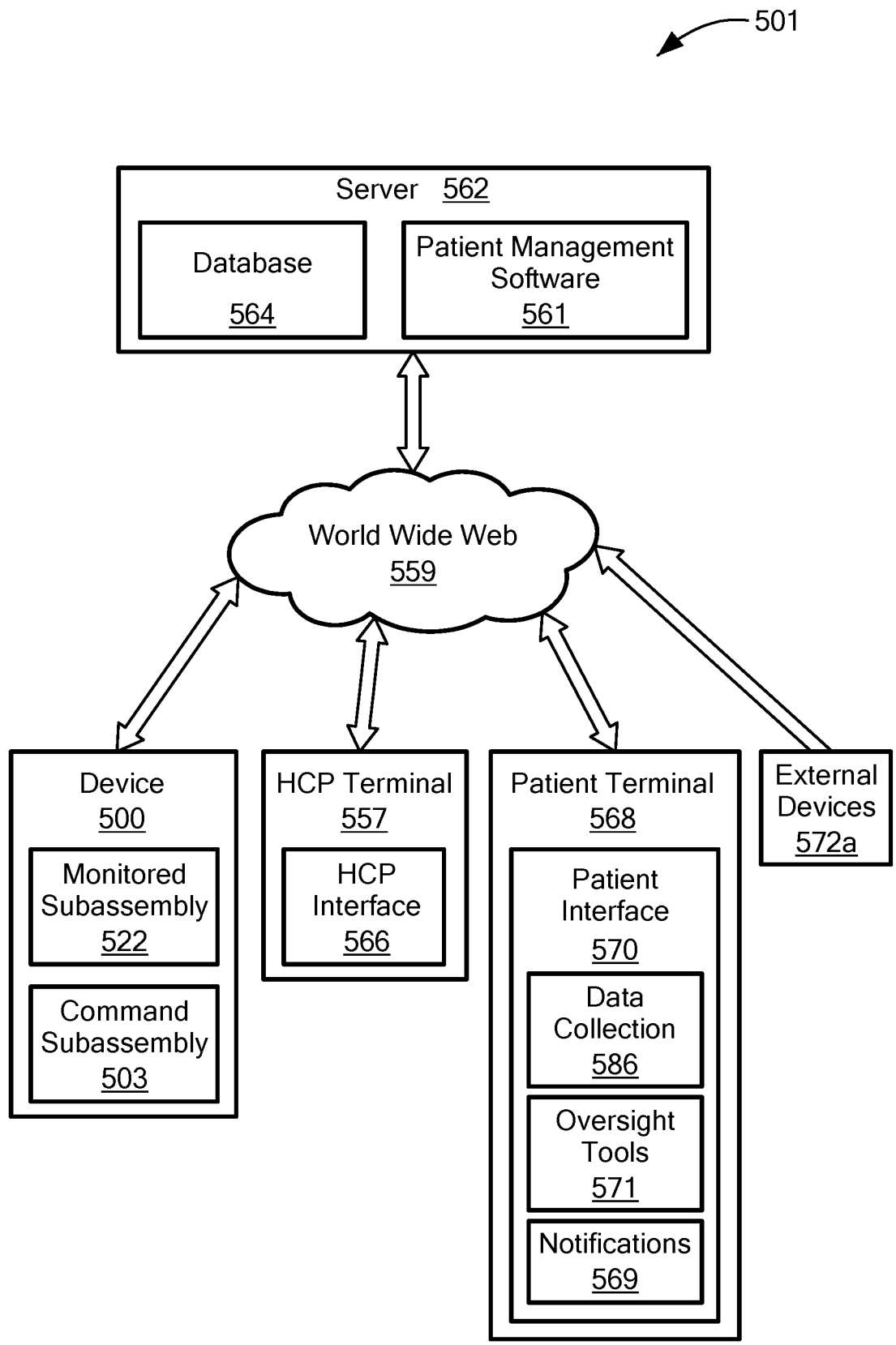
FIG. 5B is a schematic diagram of one embodiment of the information and data flow through a system of the present invention.

The distributed functional components of the present invention are described in greater detail with reference to FIG. 5B. FIG. 5B is a schematic diagram of information and data flow through system 501. In this illustrative arrangement, the communications occur over the World Wide Web 559. It should be appreciated, that although not illustrated, each communicating component may be communicating through a local area network, wide-area network, internet service provider network, and the like, implementing whatever communications technology and protocols required by that network.

The descriptions below address the functionality of certain distributed components and the communication of commands, device and patient parameters, and other data and information between such components. The structural and functional elements of these components which provide them with the capability to communicate remotely over one or more types of networks implementing various network protocols are not described herein as such hardware and software components are well-known in the art.

It should also be appreciated that components of the present invention implement security protocols via dedicated or integrated hardware/software security modules to protect the confidentiality of patient medical records. Such security measures are mandated by federal, state and local laws and regulations, as well as health care provider policies. The scope of such security measures encompass, for example, the distribution and storage of patient data, access to patient medical records including device parameters of the specific device 500 utilized by a patient, encryption of communications, validation of individual identities as a condition precedent for granting access to any component in system 501, and so on. In some embodiments of system 501, confidential patient data in the database 564 on server 562 may be anonymized, with identifying information stored locally on the doctor's terminal 557, and/or patient's smartphone 568, for additional security and privacy. It should be understood that the implemented security features change over time as the pertinent laws, regulations and policies change, and as technology and the characteristics of security threats change. Such functionality is not described further herein.

It should be appreciated that aspects of the present invention are anticipated to be implemented in software suitable for executing on general purpose computing platforms operating under the control of any commercially available or proprietary operating system. It should be understood as well that the functional modules described herein as being located on one component or another is for ease of description only and that the functionality described may be distributed across two or more communicating components in system 501.

It should also be appreciated that the functionality described herein may be implemented in software, hardware, or combinations thereof. Thus, the options available in alternative embodiments to allocate the described functionality across hardware and/or software platforms is not described further herein. The described functionality may be implemented as specified or understood to those of ordinary skill in the relevant arts.

As noted above and as shown in FIG. 5A, device 500, remote HCP 592, patient 594, and external smart devices 572a communicate directly with server 562 which is potentially located remotely from each such communicating component. Also noted above and shown in FIG. 5A, monitored device and patient parameters 588 generated by device 500, patient 594 and external smart devices 572a are transmitted over a network to remote server 562 for processing, storage and presentation to HCP 592. Conversely, HCP reviews patient and device parameters, and other patient data or information stored on server 562, and controls device 500 through the creation and transmission of regulatory commands 590 by server 562. For clarity, this architecture is maintained in the following description of FIG. 5B. It should be appreciated, however, that other architectures may be implemented in alternative embodiments.

Referring now to FIG. 5B, a functional block diagram of medication self-administration device 500 is shown. Device 500 includes two functional components relevant to this description: monitored subassembly 522 and command subassembly 503, both of which are described above with reference to FIG. 5A.

Briefly, then, monitored subassembly 522 contains sensors, detectors, etc., the outputs of which are used by subassembly 522 to determine the operational state of regulated subassembly 506 and delivery interface 504, which patient control commands 553 have been applied to delivery interface 504, and to measure the quantity of medication contained at one or more locations in device 500. Monitored subassembly 522 also gathers data from any on-board biometric device(s) 530a and on-board user-identifying devices 543a used by the patient.

Monitored subassembly 522 may also have means for accessing the electronics and memory of any such sensor, detector, etc. to retrieve such device or patient data. Monitored subassembly 522 may process the above data given that the type and format of communications used to transmit such data may be specific to the implemented components in regulated subassembly 506, display interface 504, etc., and may also be specific to the implemented sensors, detectors and the like.

Furthermore, monitored subassembly 522 is configured to interpret such information to determine the values of certain device and/or patient parameters. Such device and patient parameters are transmitted to patient management software 561 executing on server 562 via the internet, as described above. Similarly, command subassembly 503 of device 500 generates signals to control regulated subassembly 506 in response to regulatory commands generated by HCP 592 and transmitted to device 500. The outputs of command assembly 503 may take on any form suitable for the controlled components. For example, command subassembly 503 may generate electronic signals, may shift the voltage on certain input pins of a component, may write data to a microcontroller memory of a component, and so on.

System 501 also includes a patient interface 570 executing on a patient local platform 568. To provide patients with a simple and easy way to access their personal data regarding their use of device 500, as well as to provide information to their physicians, a patient interface 570 is implemented in a terminal, computer, smartphone or other platform 568 local to the patient. In one embodiment, patient interface 570 is implemented in companion application 573 introduced above with reference to FIG. 5A.

A patient data collection function 586 is preferably included in patient interface 570 to provide displays, questions and prompts, data entry fields, file attachment capabilities, and the like to receive subjective data entered by the patient. This includes, for example, patient feedback 523 regarding the medication administered using device 500, side effects, and other medical issues such as relative timing of using device 500 and the administration of other medications, food, etc. Biometric data 537 gathered by the patient is anticipated, and various displays to prompt and receive such data is also provided in embodiments of patient data collection 586. This information is provided to patient management software 561 executing on remote server 562. Patient data collection preferably includes prompts requesting the patient to confirm the successful administration of the prescribed medication as well as any problems administering the medication. In some embodiments, a health survey is displayed automatically after confirmation of successful administration is provided by the patient. In other embodiments, and more generally, patient data collection 586 periodically displays a health checkup form to update the patient's physician with the patient's current medical conditions to enable the physician to optimize treatment.

Patient interface program 570 preferably includes a program module 571 that implements oversight tools which facilitate the proper and safe use of device 500. Such tools can include, for example, timers counting down to time of next dose, automatic calculators that determine remaining doses, timing between doses, an emergency call button on each page; a log of future and past administrations; a calendar showing doses as well as calls and appointments with the doctor; a contact page with buttons for contacting the prescribing doctor, the pharmacy, and device customer service. The information utilized and presented by oversight tools 571 is obtained from patient management software 561 on server 562.

Patient Interface 570 preferably also includes patient notifications 569 to to present urgent, important, or otherwise helpful alerts, notices and the like on patient terminal 568. Instructions to display patient notices are transmitted to patient self-management interface 570 by patient management software 561 executing on server 562.

System 501 may include means for utilizing patient-related data generated by external devices 572a, described above with reference to FIG. 5A. If the physician deems it necessary to monitor additional or alternative conditions of patient 594, system 501 may include the ability to access the patient-related data generated by external devices 572a. External devices 572a may include but are not limited to devices that can measure blood pressure, pulse rate, blood oximetry, etc., and/or perform tests such as a breathalyzer test to ensure the patient can safely take the prescribed medication. External devices 572a may also include a global positioning system tracker, camera, etc. It should be appreciated that such patient-related data may be obtained directly from external devices 572a or indirectly from network-accessible system or memory associated with external devices 572a.

For HCP 592 to remotely monitor patient 594 and control device 500, embodiments of system 501 include HCP interface program 566 executing on terminal 557 or executing on server 562 and accessible via a web-based portal by physician 592 via terminal 557. Such access may be available to the doctor, pharmacist, or any other HCP 592 who may need to exercise remote monitoring, remote control, device programming or device filling functions.

Executing on server 562 is a patient management software 561 which accesses patient medical records and device status database 564. Patient management software 561 performs remote monitoring functions performed by patient management software 561 include receiving and processing monitored device parameters and monitored patient parameters transmitted by device 500 over the internet. Such information is stored and formatted for presentation to HCP 592 via HCP interface 566, and for presentation to patient 594 via patient interface 570. Remote regulation functions performed by patient management software 561 include receipt of HCP impetus at HCP interface 566 regarding the control of device 500, and transmitting such device regulatory commands 590 to device 500.

Patient management software 561 receives, processes and collocates all patient biometric data 572b received from external devices 572a, input biometric data 537 from patient interface 570, and biometric data 530b from device 500. Patient management software 561 also contains means for drawing inferences regarding a patient's medical condition based on information provided by other external devices that are not biometric devices alone or in combination with the noted biometric data. All this information is stored in patient database 564 for subsequent retrieval and presentation and presented to HCP 592 via HCP interface 566. Patient management software 561 preferably includes means for determining whether the patient biometric data and other medical information, in sum, reveals a condition or situation that warrants timely involvement of HCP 592.

Patient management software transmits device and patient data to patient interface 570 and HCP interface 566, and receives commands and data provided by the patient and HCP via the same interfaces.

It should be appreciated that patient management software 561 may be integrated with other systems to facilitate communications and data transfer with the patient and HCP. Such systems include email, text services, video conferencing, and the like.

As one of ordinary skill in the art understands, server 562 may be any networked server now or later developed which is communicably coupled to internet 559. Also, the range of information being exchanged throughout the system 501, all of which passes through the server 562, may include but is not limited to the information depicted in FIG. 5B. This information is processed by patient management software 561 and stored in database 564. Should the patient indicate a need to communicate with HCP or should patient management software 561 determine, based on the information presented alone or in combination with other information in system 501, patient management software 561 generates and transmits a message to HCP 592 indicating that the recent information provided by the patient warrants immediate review. Patient management software 561 can also generate and transmit commands based on analysis of data received, for example a shut-down command 549 upon tamper detection 524*b*.

FIG. 1 is a schematic block diagram of an exemplary embodiment of medication self-administration device 500, referred to herein as medication self-administration device 100. Device 100 is configured to deliver a prescribed medication in the form of an aerated mist into the nasal passage of a patient using the delivery method of a spray nozzle.

Given its intended use, device 100 has an exterior housing 102 configured to be held in one hand by a typical patient 594 and operated by that patient using that same hand. Various embodiments of housing 102 include ergonomic features to facilitate patient control of device 100. It should be appreciated that this is due to the particular delivery site for the medication, and that other embodiments of the device need not be configured similarly. Preferably, exterior housing 102 also has sufficient structural integrity to withstand a range of anticipated forces (type and magnitude) which may be applied to device 100 to gain unauthorized access to a prescribed medication stored therein, as well as to detect leakage, gaseous escape, sudden changes in quantity, and so on.

Delivery interface 104 is, as noted, a manually-controlled spray nozzle. As will be described in detail below, patient 594 operates delivery interface 104 via patient control actions 553 which, in this embodiment, comprises one or more manual depressions of spray nozzle 104 each causing delivery interface 104 to draw medication from a reservoir in device 100 and apply 583 the medication to the nasal cavity of patient 594. Multiple such depressions/applications may be necessary to apply an entire administered dose 582.

Recall that regulated subassembly 506 generally includes those components of device 500 which securely store prescribed medication 576 and precisely provide delivery interface 504 with a metered dose 512 of medication in accordance with remote commands provided by HCP 592. Some aspects of regulated subassembly 506 comprise two distinct yet coupled medication-holding chambers. Such embodiments of regulated subassembly 506 are referred to herein as having a dual chamber configuration.

In the exemplary embodiment illustrated in FIG. 1, device 100 has a dual chamber configuration. Specifically, in this illustrative embodiment, device 100 has two compartments for storing a prescribed medication: a secure, relatively larger, primary chamber 108 fluidically coupled to a relatively smaller, accessible metered chamber 110. Primary chamber 108 is not accessible to delivery interface 106 nor patient 594.

Primary chamber 108 is constructed and arranged to provide a hermetically sealed and tamper-resistant reservoir for storing a prescribed medication. Primary chamber 108 is configured to be refilled by pharmacy 551 via hatch 132, if necessary, and has a volumetric capacity sufficient to hold a predetermined quantity of the medication which may safely be possessed by the patient over an extended period of time while being accessible to the patient only in the limited and controlled manner as described herein.

This predetermined quantity of medication is at least the quantity reflected in full Rx supply 576 of prescribed medication described above with reference to FIG. 5A. Embodiments of hatch 132 include electromagnetic, motorized and/or physical locking mechanism. Such a hatch lock/release mechanism is configured to be controlled remotely by HCP 592, as described above, or hatch 132 may be configured to be controlled directly by, for example, pharmacy 551. In the same or alternative embodiments, primary chamber 108 has a structurally reinforced design that enables the chamber to prevent leakage and withstand attempts of penetration under any reasonable impact or other force.

Metered chamber 110 is configured to store the maximum potential dosage of the prescribed medication for ultimate transfer to delivery interface 104. Metered chamber 110 is configured to be accessible by delivery interface 506 as described herein. As will be described in detail below, in a dual chamber configuration, a specified amount of medication, at the specified time, is transferred from primary chamber 108 to metered chamber 110, allowing the patient to activate the delivery interface to administer the medication in the metered chamber. Fluidic tubing or a needle outlet 148 extends from an opening in the metered chamber or any location where the entirety of fluid volume dispensed into it by the pump is accessible. Embodiments of the metered chamber are configured to prevent access to the medication that is located upstream (not yet transferred, i.e. not intended for current dose) of this chamber.

As noted, primary chamber 108 and metered chamber 110 are fluidically connected to each other. This fluid path 114 consists of suitable tubing. In other embodiments, the two chambers are contained in a single housing and are fluidically coupled via channels in a substrate.

In response to dose quantity command 545 and dose schedule 547, a single dose is transferred from primary chamber 108 to metered chamber 110 via fluidic tubing 114 by a fluid transfer mechanism in form of pump 112. The device makes a precise dose available and nothing more, and the medication transfer mechanism is responsible for transferring this precise dose into a location accessible to the delivery interface 104 and hence the user. In the embodiment of the device in FIG. 1, this mechanism takes the form of a fluidic pump, which, on schedule 547 set by the HCP, pumps precisely one dose from the Primary Chamber 108 into the Metered Chamber 110.

Pump 112 is any pump now or later developed that precisely and accurately transfers fluid. The pump type may differ between embodiments, with some possibilities including peristaltic, piezoelectric, syringe, and solenoid pumps. Embodiments of the pump may or may not serve the additional purpose of a one-way valve. In some embodiments, one or more one-way valves may be implemented, as may one or more physical locking mechanisms, to restrict upstream flow and to restrict access to the Primary Chamber 108.

In the above description of the embodiments illustrated in FIG. 1, chambers 108 and 110 are referred to as having a fixed volumetric capacity. It should be appreciated, however, that in alternative embodiments, either or both chambers are configured to have an adjustable volumetric capacity.

The components of the fluidic subassembly can be spatially configured in any way in order to minimize size and optimize performance. In alternative embodiments one or both of the primary and secondary reservoirs may be adjustable to accommodate a particular medication prescription and desired duration between refills. For example, in one embodiment, the interior surface of one wall of the reservoirs is adjustable by pharmacy 551 or HCP 592 via a volumetric control interface on the device. In certain embodiments, manually adjusting the control interface to one of a few available settings permanently changes the position of the adjustable interior wall. Interlocking features prevent further adjustment. In another embodiment, the reservoirs include a bladder and the volumetric capacity of the bladder is adjusted by the HCP by limiting the expansion of the bladder such as, for example, by filling the interstitial space between the bladder and the interior surface of the reservoirs. In an alternative embodiment, each reservoir is one of a set of reservoirs all having the same form, fit and function but each having a different volumetric capacity.

The embodiment of monitored subassembly 522 of device 100 comprises a tamper sensor 124a and an administration event sensor 126a. Tamper sensor 124a is configured and arranged in device 100 so as to detect unauthorized attempts to access regulated subassembly 106. Implementations of tamper sensor 124a include but are not limited to, capacitive, resistive, or piezoelectric sensors arranged in device 101 to detect applied forces. Other embodiments of tamper sensor 124a detect light or air entering a part of device 100 normally isolated from the outside environment.

Administration event sensor 126a is configured and arranged to detect when patient 594 is using device 100 to self-administer the medication. Embodiments of sensor 126a include but are not limited to, a contact sensor within the spray nozzle Delivery Interface 104, fluid level sensor within metered chamber 110, or biometric sensor to detect expected biometric changes accompanying a dose. Another embodiment of sensor 126a is a camera structure and arranged to capture images of patient 594 administering the medication or performing some test or act. The electronic subassembly is configured to wirelessly receive commands and to execute such commands, as well as to wirelessly transmit sensor data to the server. The storage, processing, and transmission of data is all designed and executed in accordance with government regulations. A wireless transmitter/receiver receives remote commands (e.g. aliquot dose or unlock refill hatch) and sends them to a microcontroller, which processes them and outputs the necessary signal to the associated subcircuit for execution. Sensor data is recorded by the microcontroller, which then sends it to the wireless transmitter/receiver for transmittance to the paired device/server.

Device 100 is powered through any current or future method, called herein the power source 116. Some possible embodiments of the power source include but are not limited to a disposable battery, a rechargeable battery, a power cord directly to a wall outlet, USB charging port, and wireless charging coil. The entire electronic subassembly is supplied with direct current from a power source 116, which supplies power to each electronic component needing it.

Figure 2:
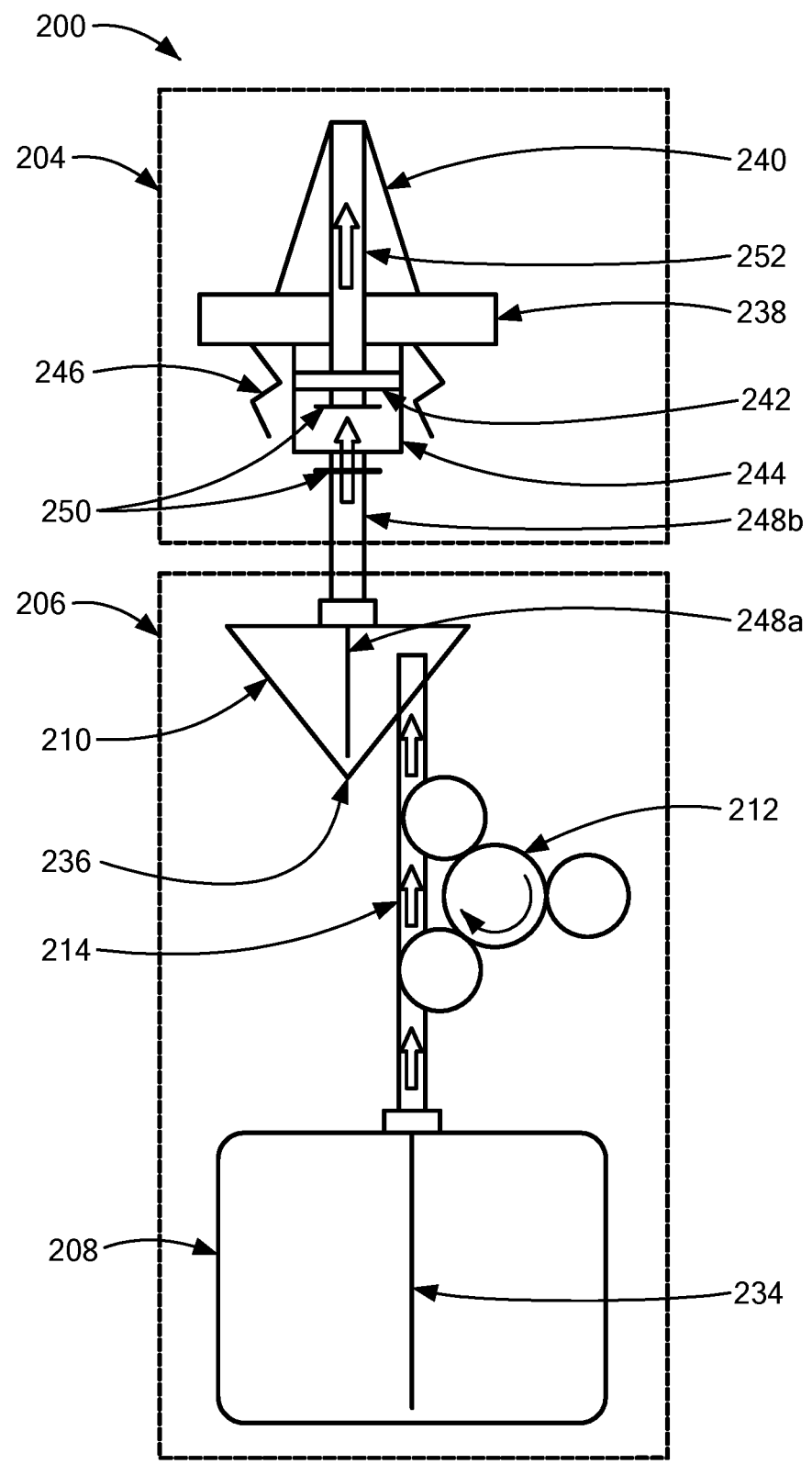
FIG. 2 is a schematic block diagram of one embodiment of a dual-chamber nasal spray delivery device.

FIG. 2 is a schematic block diagram of one embodiment of dual-chamber nasal spray delivery device 100, referred to herein as device 200. Device 200 includes a regulated subassembly 206 fluidically coupled to a delivery interface 204. Regulated subassembly 206 has a dual chamber configuration, comprising primary chamber 208 fluidically coupled to metered chamber 210 via a pump 212.

In the embodiment illustrated in FIG. 2, primary chamber 208 has a secure, hermetically sealed port of connection with a tube 214 which fluidically couples primary chamber 208 and metered chamber 210. Fluidic tubing 214 is coupled to a needle 234 which extends through primary chamber 208, terminating at a location which ensures all of the medication stored in primary chamber 208 is retrievable for transfer to metered chamber 210. In some embodiments, needle 234 is an integrated component of primary chamber 208 while in other embodiments it is a unitary feature of primary chamber 208. In some embodiments, the interior surface of primary chamber 208 opposite the port side of the chamber is configured to facilitate uptake of the medication by needle 234.

Pump 212 is constructed and arranged to transfer medication from primary chamber 208 to metered chamber 210, and in this embodiment is a peristaltic pump 212, through which tubing 214 passes. Peristaltic pump 212 is a form of positive displacement pump, and works by utilizing a carousel of cylinders, at least one of which is always in contact with and pressing flat tubing 214, restricting flow at that pinch point. When pumping, this carousel rotates about its central axis, driven by an electric motor, and the cylinders rotate around this central axis with it, as well as on their own individual rotational axes to reduce friction with tubing 214. The pinched point on tubing 214 is hence moved forward along the tube, pushing with it the fluid above the pinch point, and creating a suction which draws up more fluid. By the time the uppermost pinch point is released, the next cylinder has already pinched a lower point in the tube. This rotational motion of the carousel therefore transfers a quantized volume of fluid with each revolution.

The medication advanced by pump 212 continues through tubing 214 into metered chamber 210. As noted, the medication stored in metered chamber 210 is accessible to delivery interface 204. An extraction needle 248a extends from an outlet port at the top of metered chamber 210 to the opposing, bottom surface of the chamber, for example the metered chamber's nadir 236. In this embodiment, the bottom interior surface is concave, facilitating the accumulation of medication in metered chamber 210. When device 200 is held in its application/delivery orientation, the medication will accumulate at the nadir 236 of the concave surface. In such embodiments, the fluidic tubing or needle 248a extends through metered chamber 210, terminating immediately above nadir 236.

In other embodiments, the interior surface(s) of either chamber and/or tubing (208, 210, 214, 234, 248a, 248b) include channels, coatings, etc. optimized for the viscosity and other properties of the medication to facilitate the fluidic transport of the medication through device 200. The fluidic tubing provides a hermetically sealed, tamper-proof and sterile passage between primary chamber 208 and a fluidic pump.

As noted above with reference to FIG. 1, medication delivery interface 104 is a manually-controlled spray nozzle configured to draw medication from a reservoir in device 101. Patient 594 operates delivery interface 104 via patient control actions 553 which, in this embodiment, comprises the manual depression of spray nozzle 104 causing an application 583 of medication to the nasal cavity of patient 594. Multiple such depressions may be necessary to apply an entire administered dose 582.

This illustrative embodiment of spray nozzle 204 includes a spray chamber 244 having a capacity to retain a volume of prescribed medication ideal for uptake by the nasal mucosa in a single application or administration 583 of the medication.

A rounded nasal cone 240 with a capillary 252 from the center of its base through its tip serves as the nozzle, and is designed to fit well in a common nostril and spray a medication particle array of optimal geometry. Spray capillary 252 extends through a reverse plunger piston 242, terminating in spray chamber 244. As such, there is a contiguous fluid path from spray chamber 244 through nasal cone 240 to exit the distal end of the nasal cone.

Spray chamber 244 is fluidically connected to metered chamber 210 via tubing 248b. Tubing 248b is configured to be securely attached to an access port of metered chamber 210 and metered chamber extractor tubing or needle 248a. Spray nozzle 204 includes a one-way valve 250 in extractor tubing 248b to prevent upstream, or reverse, flow of medication retained in spray chamber 244.

Device 204 is to be controllably grasped in one hand of patient 594, with the index and middle fingers resting on the flanges of nozzle depressor 238, causing nasal cone 240 to extend through the fingers. Patient control actions 533 include patient 594 depressing nozzle depressor 238, causing it to travel toward the body of device 200.

Embodiments of spray nozzle 204 include a manually-controllable reverse plunger piston 242 configured to drive the medication retained in spray chamber 244 through a spray capillary 252 as piston 242 advances through chamber 244 in response to patient 594 depressing nozzle depressor 238. medication traveling through spray capillary 252 exits the distal end of nasal cone 240 in a mist.

A spring 246 located in spray nozzle 204 applies a bias force to nozzle depressor 238. When patient 594 activates spray nozzle 204, the manual force applied to nozzle depressor 238 is sufficient to overcome the spring bias force so as to move nozzle depressor 238 toward device housing 102.

Subsequent physical release of depressor 238 enables plunger piston 242 to return to its original, retracted position due to the biasing force of spring 246. As plunger piston 242 returns to its retracted position, it creates a vacuum in spray chamber 244 sufficient to draw additional medication, if any, from metered chamber 210. A second one-way valve 250 configured and arranged to prevent air from entering metered chamber 210 via spray nozzle 204.

It should be appreciated that in some embodiments nasal cone 240 and reverse plunger piston 242 are a single, unitary unit. In other embodiments nasal cone 240 is detachable from piston 242 and is one of a set of nasal cones of various sizes and shapes, each configured to optimally fit in a predetermined class of patient nasal cavities.

Figure 3:
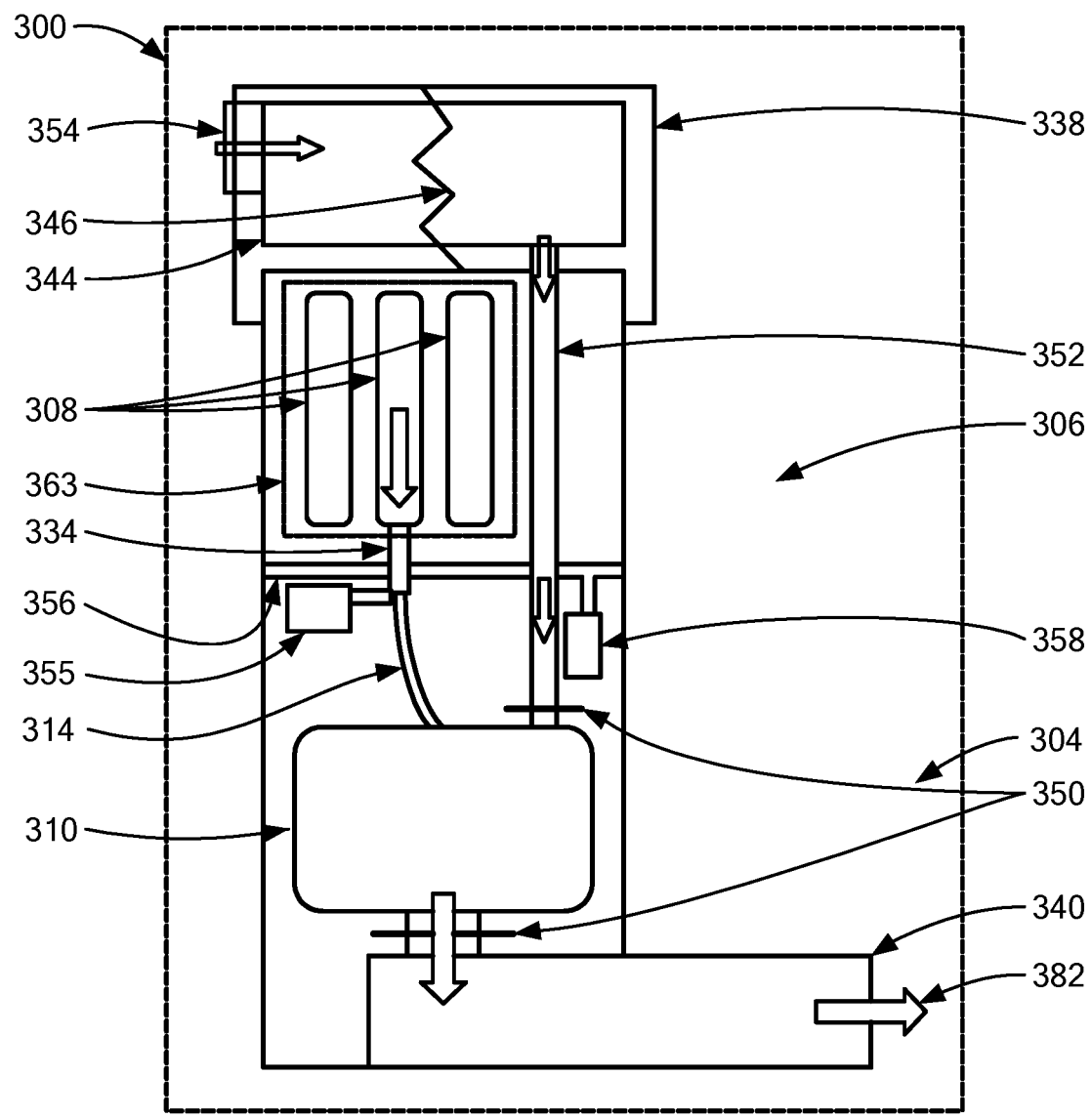
FIG. 3 is a schematic block diagram of an alternative embodiment of a medication self-administration device.

FIG. 3 is a schematic block diagram of an alternative embodiment of medication delivery device 500, referred to herein as medication delivery device 300. Device 300 is configured to provide an administered dose 382 of prescribed medication in the form of a gas using the delivery method of an inhaler for the purpose of making the gaseous medication available for inhalation by a patient. Device 300 includes an alternative embodiment of regulated subassembly 506, referred to herein as regulated subassembly 306.

Regulated subassembly 306 has a set of independent compartments, referred to herein as cartridges 308, each configured to store at least a single dose of prescribed medication. In the embodiment shown in FIG. 3, regulated subassembly 306 has three such cartridges 308. It should be appreciated, however, that any number of cartridges 308 may be implemented in alternative cartridge configurations. As will be appreciated from the description below, collectively, cartridges 308 are functionally analogous to the primary chamber in the dual chamber configurations described above. Similarly, a currently-accessed cartridge 308 is functionally analogous to the metered chamber in the dual chamber configurations described above.

Device 300 includes an alternative embodiment of delivery interface 504, referred to herein as delivery interface 304. Regulated subassembly 306 is fluidically coupled to delivery interface 304 as described hereinbelow. Delivery interface 304 contains a holding chamber 310 fluidically coupled to a selected cartridge 308 via a fluid transfer mechanism of regulated subassembly 306. Holding chamber 310 is configured to store a single gaseous dose of a prescribed medication, and to provide that medication to the patient as described below.

Said fluid transfer mechanism includes an extraction tap 334 configured to penetrate a selected cartridge 308 to initiate a fluid path between the selected cartridge and holding chamber 310. Cartridges 308 may be configured with a penetrable port while extraction tap 334 is configured to penetrate the implemented type of port. For example, in one embodiment, cartridges 308 have a silicone seal while extraction tap 334 comprises a syringe. Cartridges 308 are pressurized; that is, cartridges 308 retain prescribed medication under pressure which evacuates the cartridge when penetrated by extraction tap 334.

The fluid transfer mechanism includes a series of integrated tracks 356 over which extraction tap 334 travels. Integrated tracks 356 are proximate the array 363 of cartridges 308. Under the control of one or more motors 358, extraction tap 334 travels over tracks 356 to be positioned immediately adjacent a selected cartridge 308. Once tap 334 is aligned with selected cartridge 308, an actuator 355 advances tap 334 toward selected cartridge 308 until tap contacts selected cartridge 308. Upon contact, extraction tap 334 penetrates the selected cartridge.

Extraction tap 334 is fluidically coupled to a tube 314 the opposing end of which terminates in holding chamber 310. Thus, extraction tap 334 and tubing 314 provide a continuous fluid path into holding chamber 310.

As noted, cartridges 308 are pressurized. As such, when tap 334 penetrates selected cartridge 308, the medication contained therein is evacuated under the cartridge pressure, causing the medication to flow into holding chamber 310.

It should be appreciated that in alternative embodiments, fluid transfer mechanism 312 secures retains extraction tap 334 is a fixed position, and array 363 of cartridges 308 rotates or translates relative to extraction tap 334 to align a selected cartridge adjacent to the tap.

It should also be appreciated that in alternative embodiments, extraction tap 334 translates relative to cartridges 308, and penetrates a selected cartridge 308, in response to patient control actions rather than in response to electromechanical motors 358 and actuators 355.

Delivery interface 304 of device 300 comprises a collapsible air chamber 344 fluidically coupled to holding chamber 310 via air exit duct 352. Collapsible air chamber 344 is constructed and arranged to be manually collapsed in response to a manual force applied to a depressor cap 338. As air chamber 344 is being collapsed, air occupying the chamber is forced through air exit duct 352 into holding chamber 310, replacing and forcing the medication contained therein out of the chamber and through a mouthpiece 340 to exit the device as an administered dose 382 of the prescribed medication.

When depressor cap 338 is released, the bias force of spring 346 drives the cap back up to its original position. As depressor cap 338 returns to its default position, it causes collapsible air chamber 344 to expand, creating a vacuum that draws air into the chamber through one-way air intake duct and filter 354.

In an alternative embodiment, fluid transfer mechanism 312 provides a direct path from an extraction tap 334 to mouthpiece 340 or other delivery interface component suitable for the specified delivery method. In still other embodiments, cartridges 308 are not pressurized and the prescribed medication contained in a selected cartridge is drawn from the cartridge by delivery interface 304.

Advantageously, embodiments of medication delivery device 300 securely stores the prescribed medication unselected cartridges of cartridge array 363, which are inaccessible by the patient and the delivery mechanism. The patient only has access to the precise dose of prescribed medication stored in a selected cartridge 308, which are made accessible in accordance with the dose schedule command provided by HCP.

Figure 4:
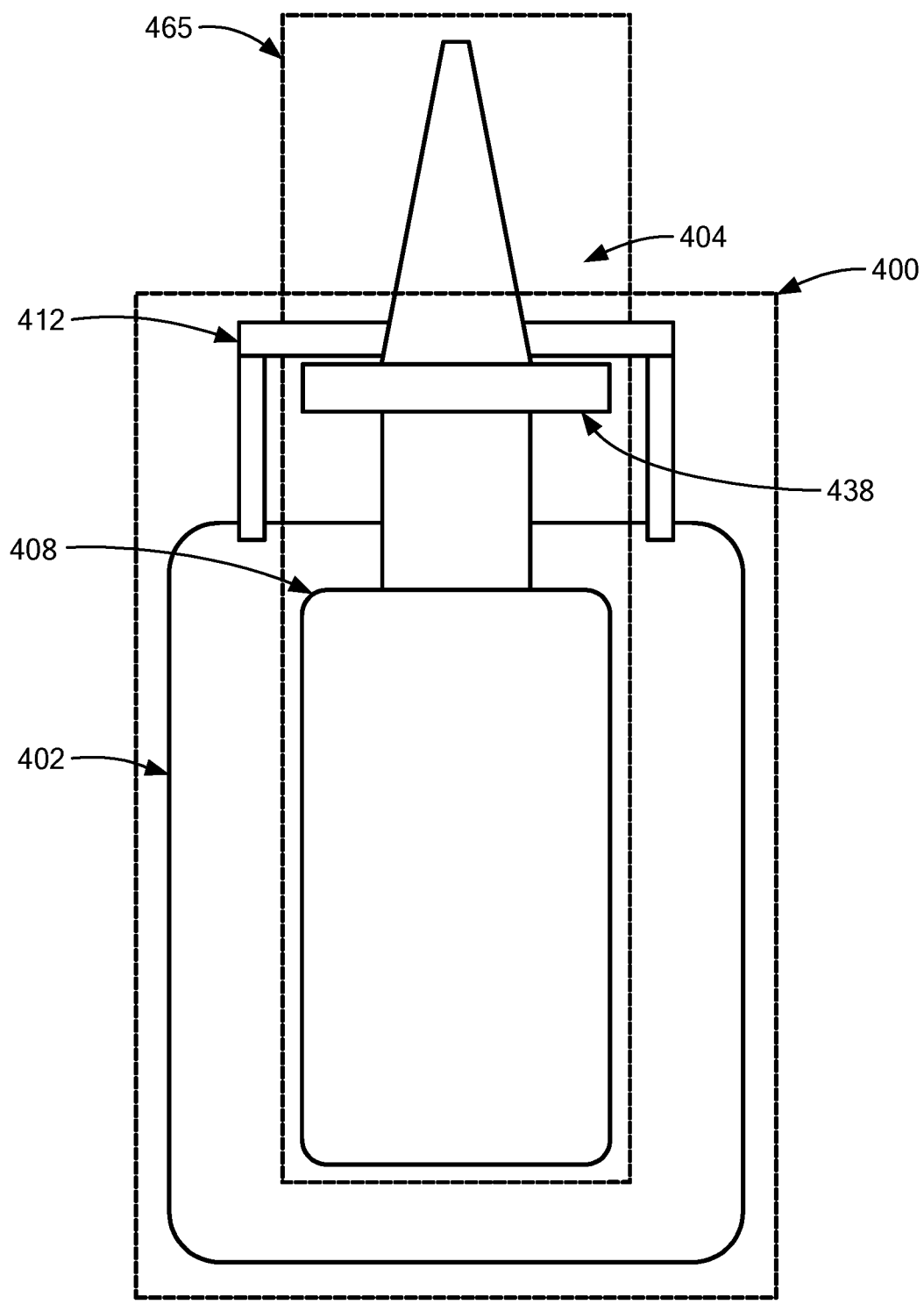
FIG. 4 is a schematic block diagram of an alternative embodiment of a medication self-administration device.

FIG. 4 is a schematic diagram of an alternative embodiment of the device of the present invention, referred to herein as having an add-on device configuration. Such an add-on device may be used in conjunction with an existing third-party medication delivery device 465 rather than as a replacement for such device. The functionality of the two devices in tandem would be equivalent to those functions described for device 500. One example of such an embodiment is a device 400 which attaches and locks onto an existing nasal spray product, and adds to it the regulating and monitoring functions of device 500. While the third-party device 465 would be storing and delivering the medication, the add-on device 400 could allow depression of the spray nozzle only a specified number of times, at specified times and dates, while also tracking administration, tampering, and more. This add-on device would be internet-connected, and have all the same functionality as device 500 beside the storage and delivery of medication.

Device 400 is one embodiment of such an add-on device, paired with 3rd-party standard nasal spray 465. The standard nasal spray 465 consists of a single chamber of medication 408 which is directly accessible to spray nozzle assembly 404. Device 400 is securely attached to device 465. Device 400 has a tamper-resistant outer shell 402 which fully surrounds chamber 408 and has built-in sensors to detect any attempt to separate the two devices. Device 400 regulates the use of device 465, including both dose quantity 545 and schedule 547, with a component 412 which encapsulates the spray nozzle depressor 438 of device 465. The ability for the user to depress the depressor and hence administer medication is determined by the state of component 412, which, utilizing an electromagnetic mechanical locking mechanism, can unlock to allow for administration, and lock to restrict administration. Device 400 further consists of a monitored subassembly and necessary electronics, including a communication module, in order for the paired devices to together have the same functionality as device 500.

The displays generated by one embodiment of patient interface 570 are illustrated in FIGS. 6A-6H. As noted, interface 570 may be implemented as a downloadable application to execute on a patient's smartphone. Such a downloadable application was introduced above as companion app 573 in connection with FIGS. 5A and 5B.

Figure 6A:
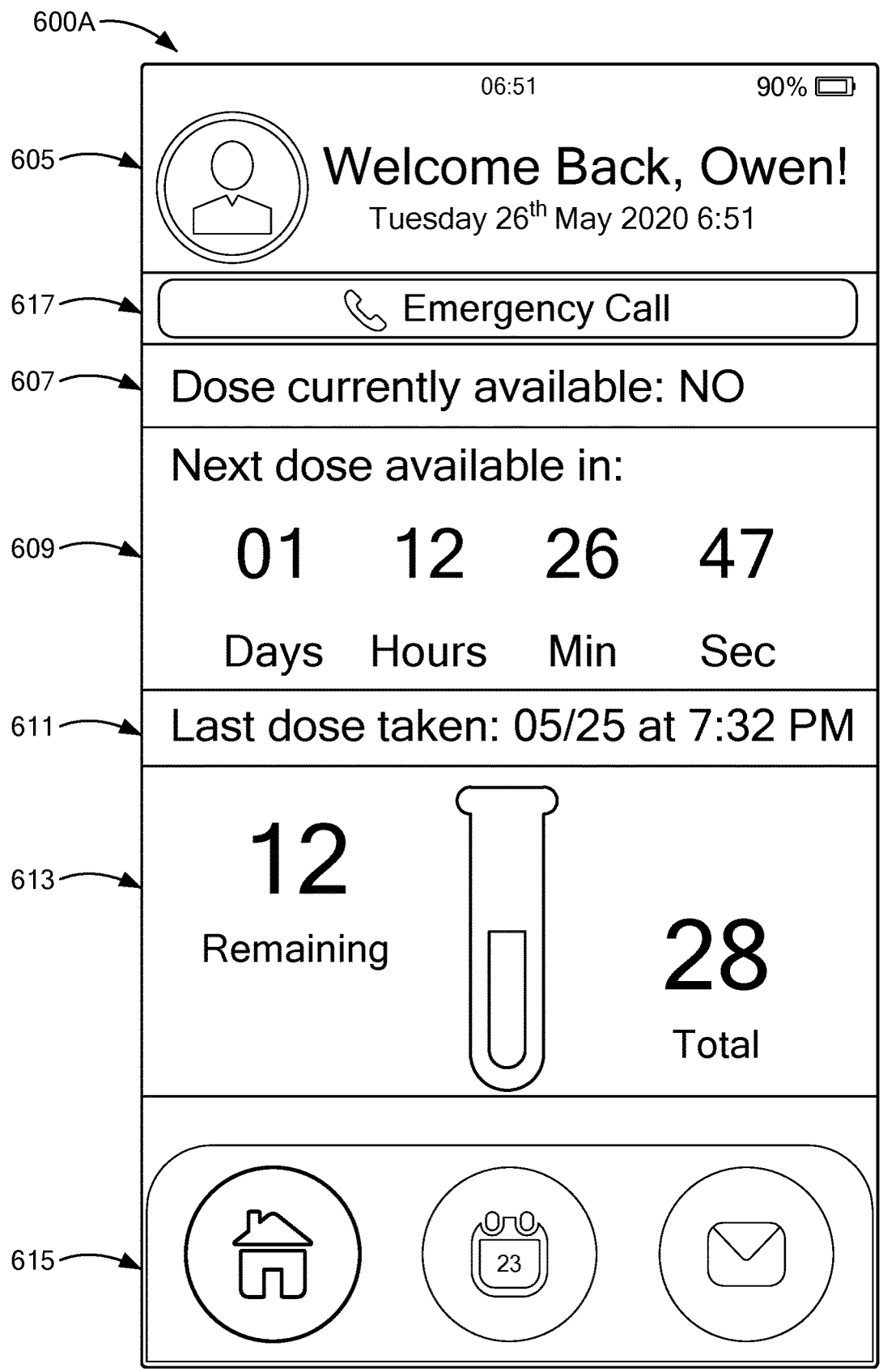
FIGS. 6A-6H are displays generated by embodiments of a patient interface of the present invention.

A home page 600A is presented in FIG. 6A. Home page 600A has a header 605 including user profile information and current time and date, as well as an emergency call button 617 which dials emergency services after the patient confirms the initial selection of the call button was intentional. Below the header is an indication 607 of whether a dose is currently available or not. Below 607 is an actively ticking countdown 609 to the next scheduled dose. Below that is indication 611 of the time and date of the last dose taken, and below that is an indication 613 of how many doses are remaining in the current prescription. At the bottom of the page is a navigation menu 615, with large buttons to navigate between the home page 600A, calendar/log page 600B/C and contact page 600D.

Figure 6B:
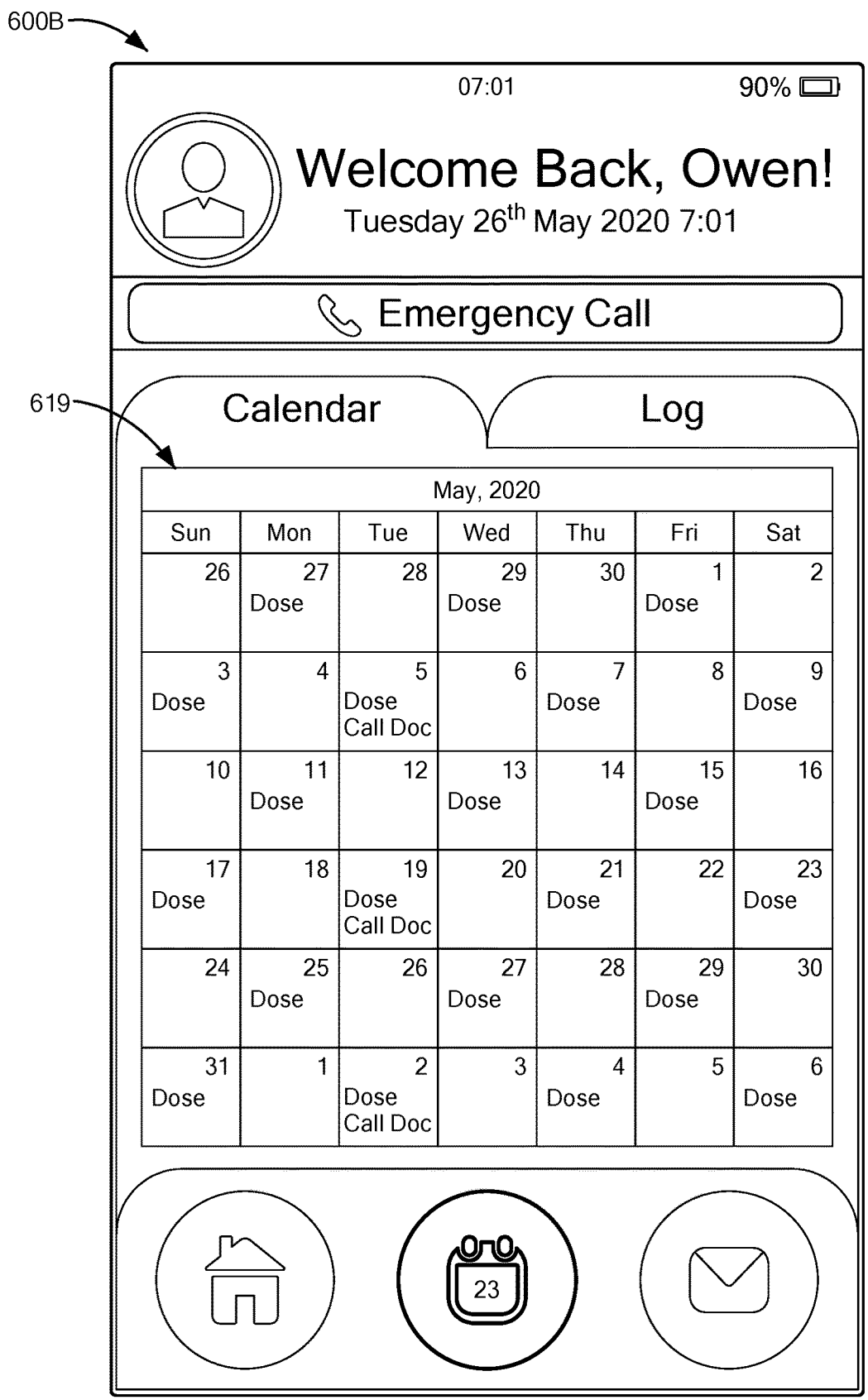

A displayed scheduling page 600B is presented in FIG. 6B. Page 600B includes a calendar 619 in addition to the same header 605, emergency call button 617, and menu 615. Calendar 619 includes doses, scheduled check-up calls with the doctor, as well as doctor's appointments.

Figure 6C:
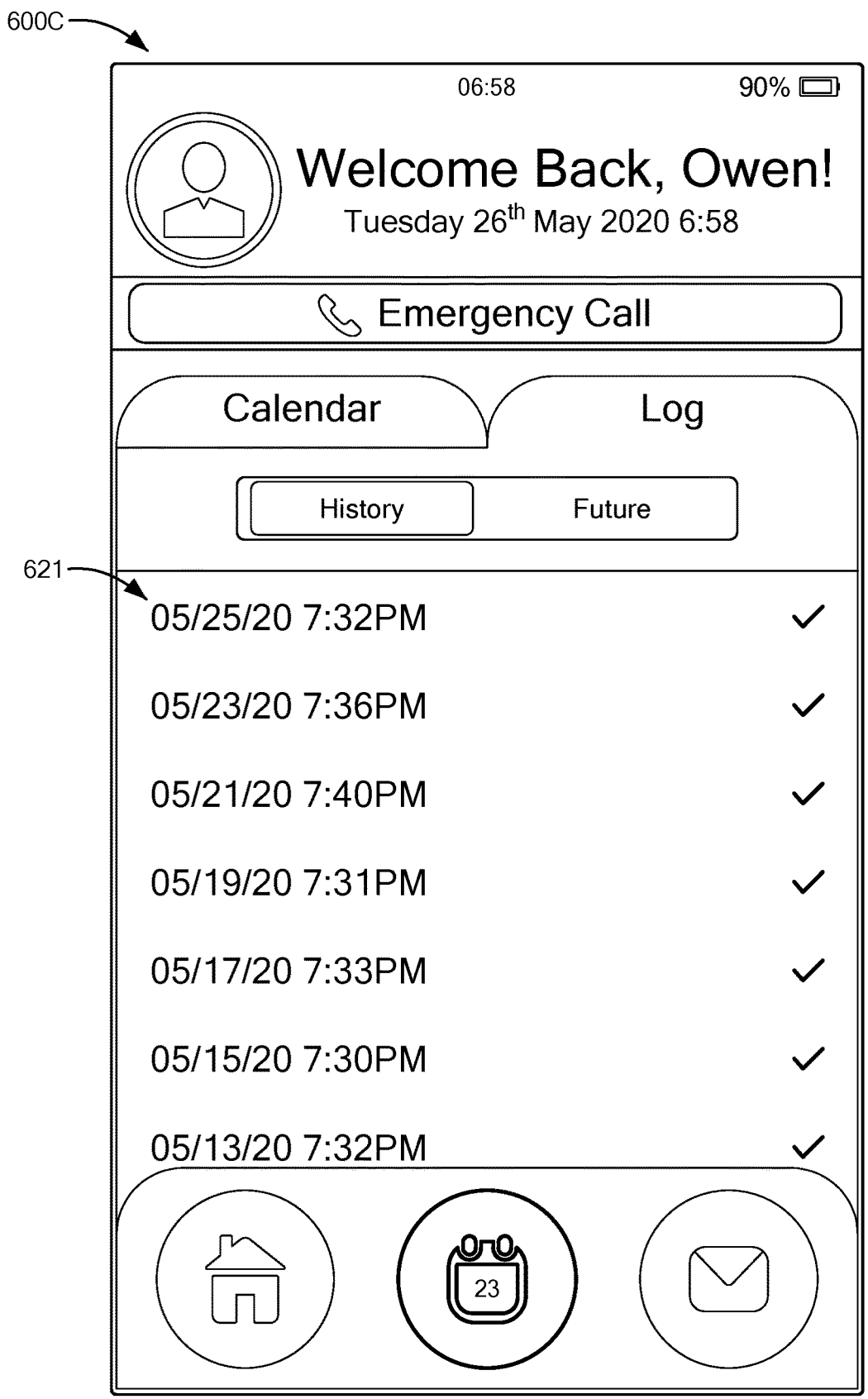

A displayed log page 600C is presented in FIG. 6C. Log page 600C includes a listing or log 621 of prior and future doses. Log 621 and calendar 619 are both within the same navigation page, which can be toggled between them.

Figure 6D:
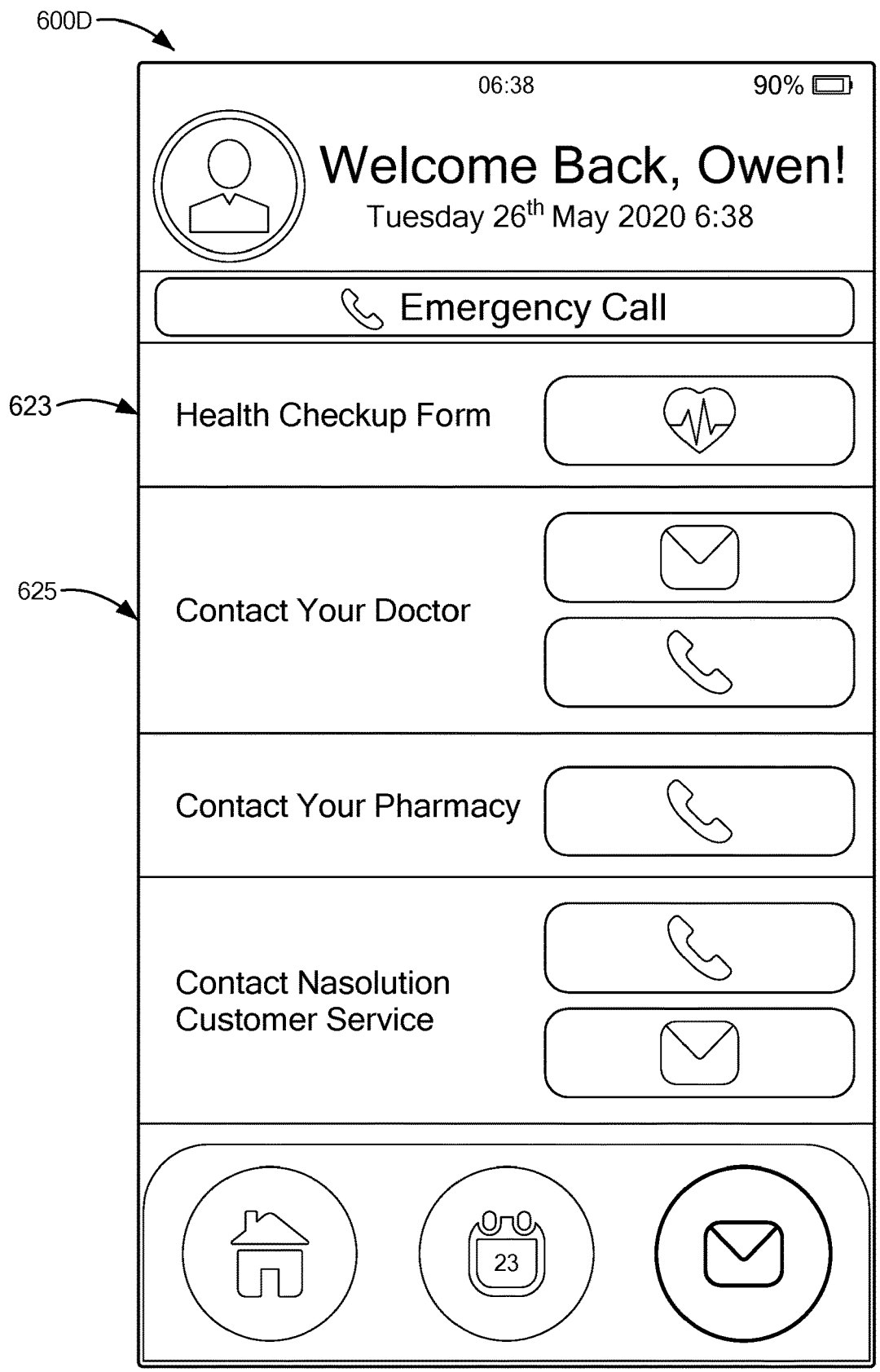

A displayed contact page 600D is presented in FIG. 6D. Contact page 600D includes the same header 605, emergency call button 617, and menu 615. In addition, a button is displayed which, when selected, brings the patient to a health checkup form 623. Form 623 has data entry fields and option selection features for the patient to input health-related data into patient interface 570, including the input of feedback 523 and biometric 537. This information is transmitted to patient management software 561 executing on server 562 for processing and storage, and for presentation to HCP 592 when appropriate.

Returning to display page 600D in FIG. 6D, below the health checkup form button is a series of contact links 625, including buttons to email and call the user's prescribing doctor, call the pharmacy from which the medication was obtained, as well as call and email the customer service for help with the device or other system component.

Figure 6E:
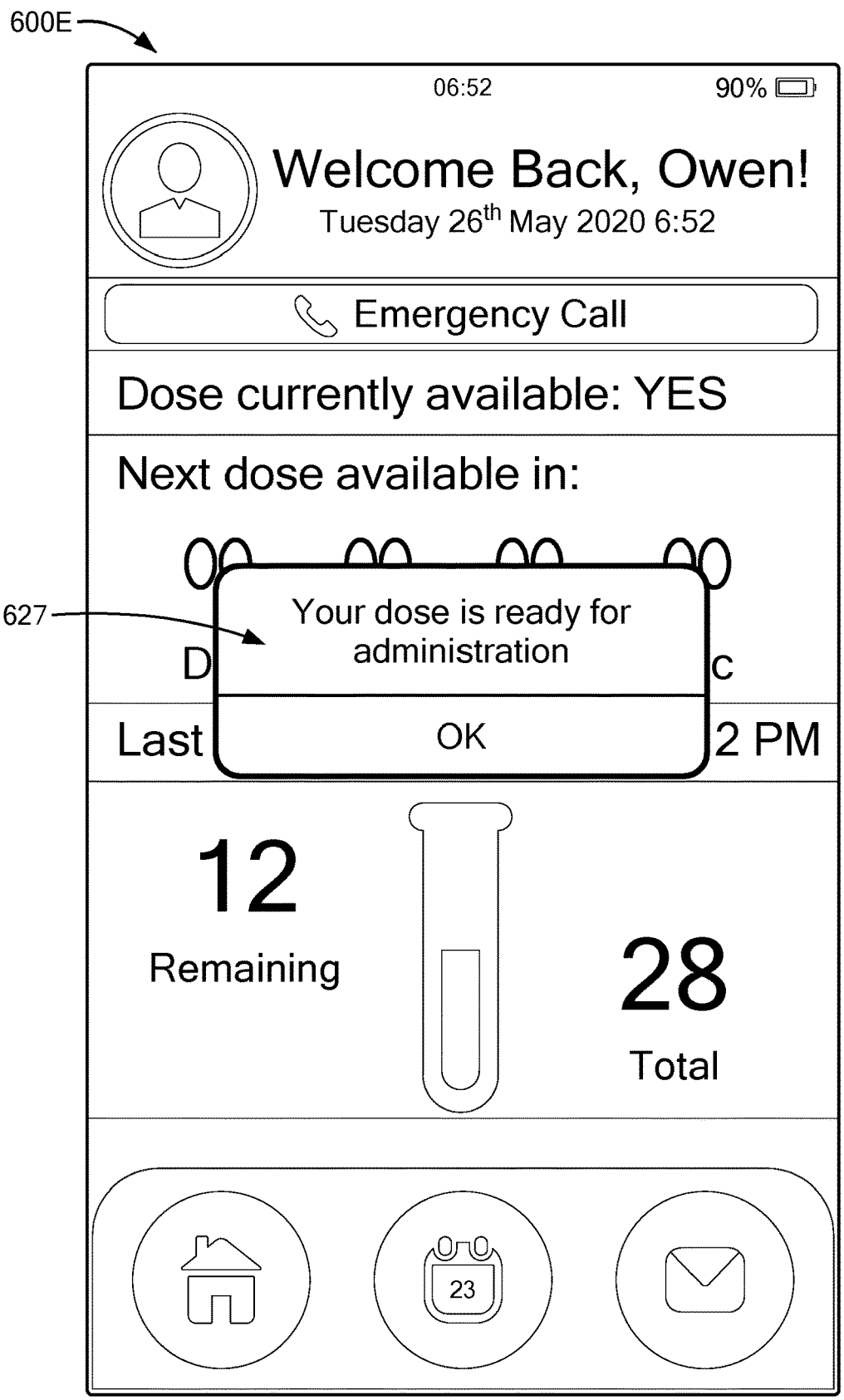

A displayed notification page 600E is presented in FIG. 6E. Page 600E includes a popup dialogue 627 indicating that a dose is ready to be administered. This popup would appear after the scheduled dose time arrives, all requirements are met, and the device makes the dose available. This popup would also be accompanied by a push notification.

Figure 6F:
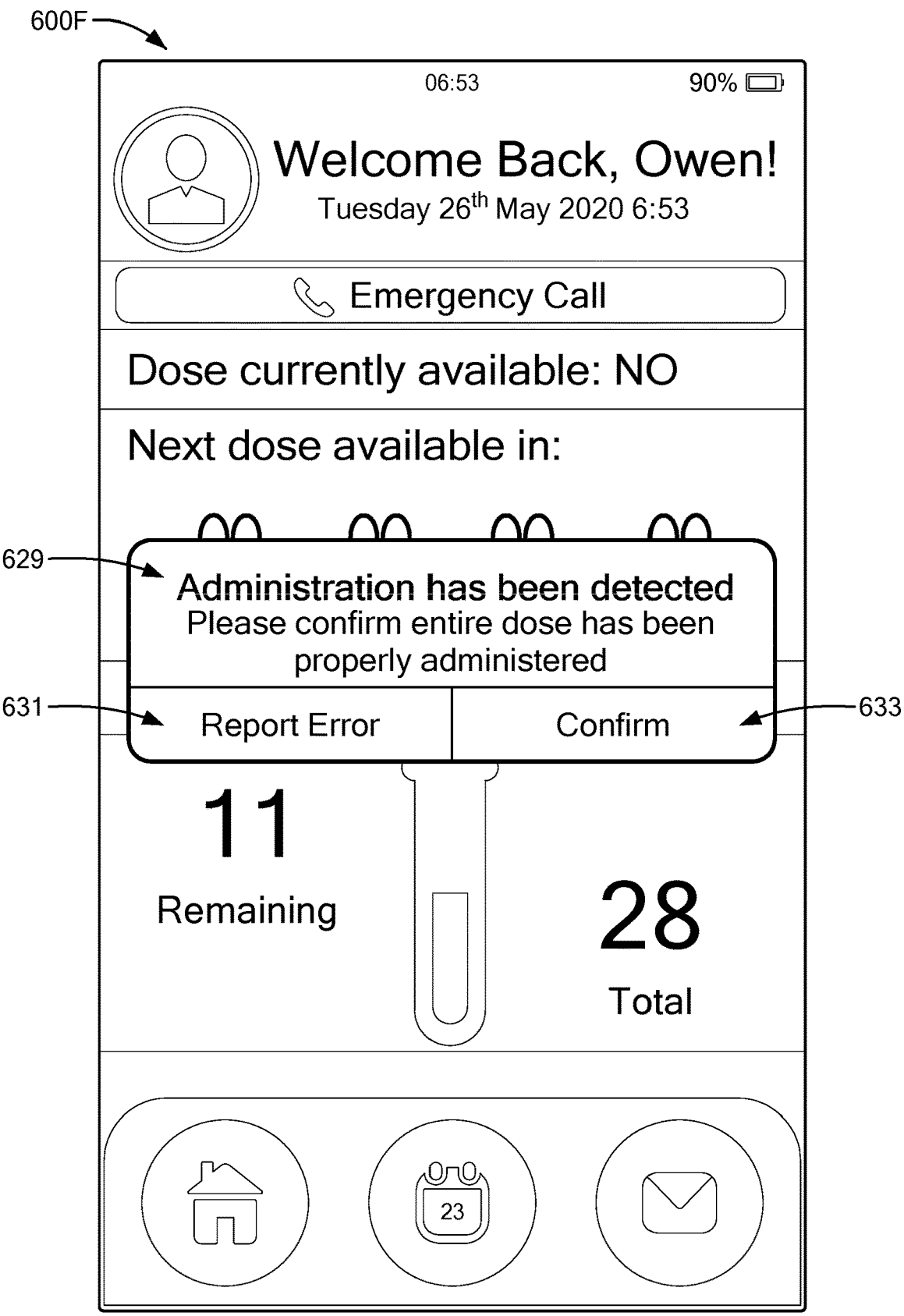

An inquiry display page 600F is presented in FIG. 6F. Page 600F depicts the popup dialogue 629 indicating that the administration of the scheduled and available dose has been detected by the device's onboard administration sensor(s). This popup requests for the user to either confirm that the dose was successfully administered 633 or report an error 631. When 631 is selected, another popup dialogue inquires about the error type and helps to hopefully resolve the problem. By selecting 633, the system is updated to reflect the successful administration, and another popup window appears asking for feedback on health and side effects experienced as well as the treatment as a whole. Such a popup may be similar or identical to health checkup form 623.

Figure 6G:
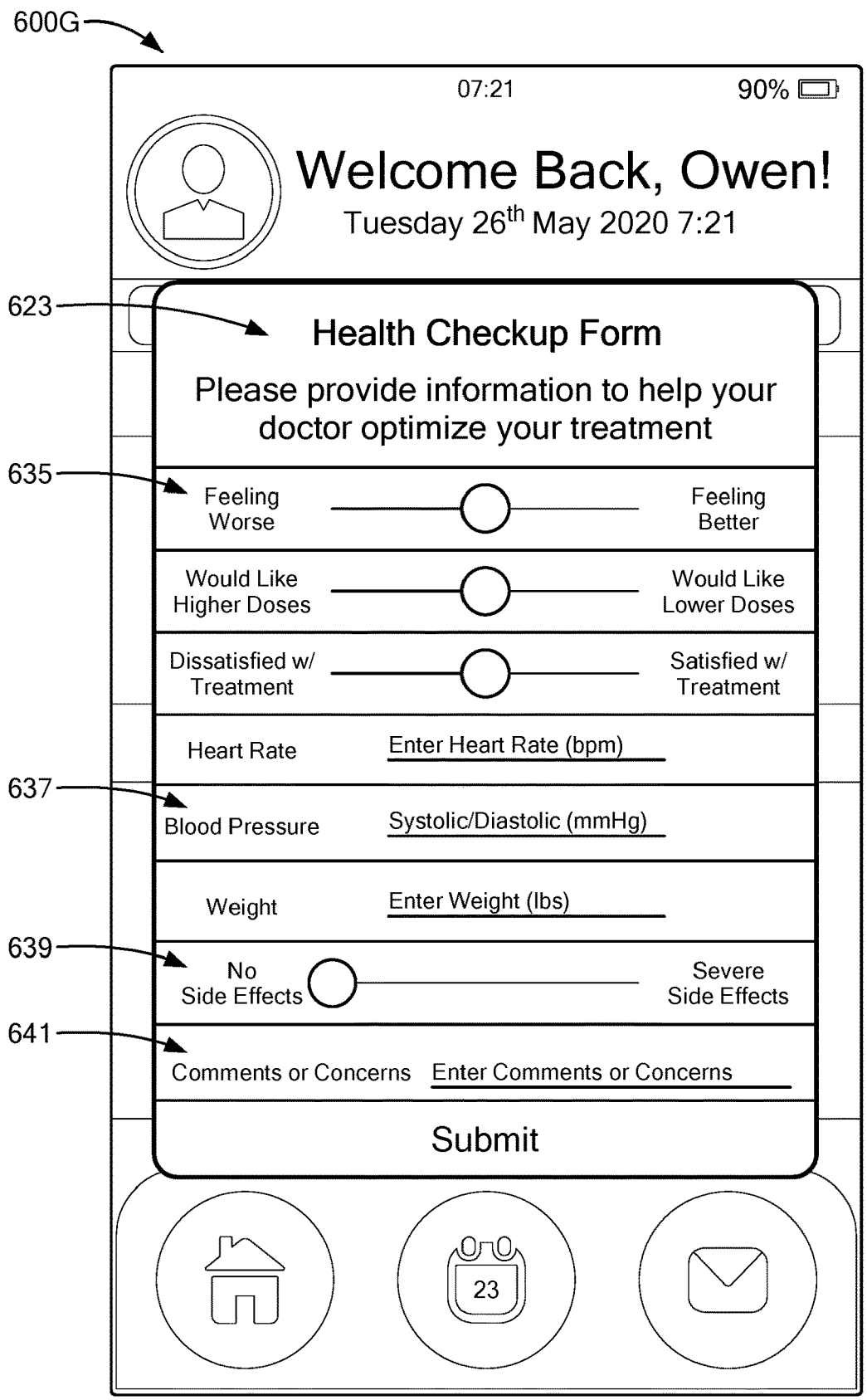

Health checkup form 623, depicted in FIG. 6G, uses slidebars 635 adjustable by the patient to reflect a rating of feeling worse to feeling better, wanting higher or lower doses, and being satisfied or not with the treatment progress. Requests for manually input biometric data 637 enable the patient to send easy to collect biometric data back to their doctor. As side effects are often a concern of doctors, 639 inquires into the severity and type of side effects, which pops up in a separate window found in F6H. Lastly, a free response comment section is supplied to allow patients to give any feedback 641 that doesn't concern one of the subjects already covered.

Figure 6H:
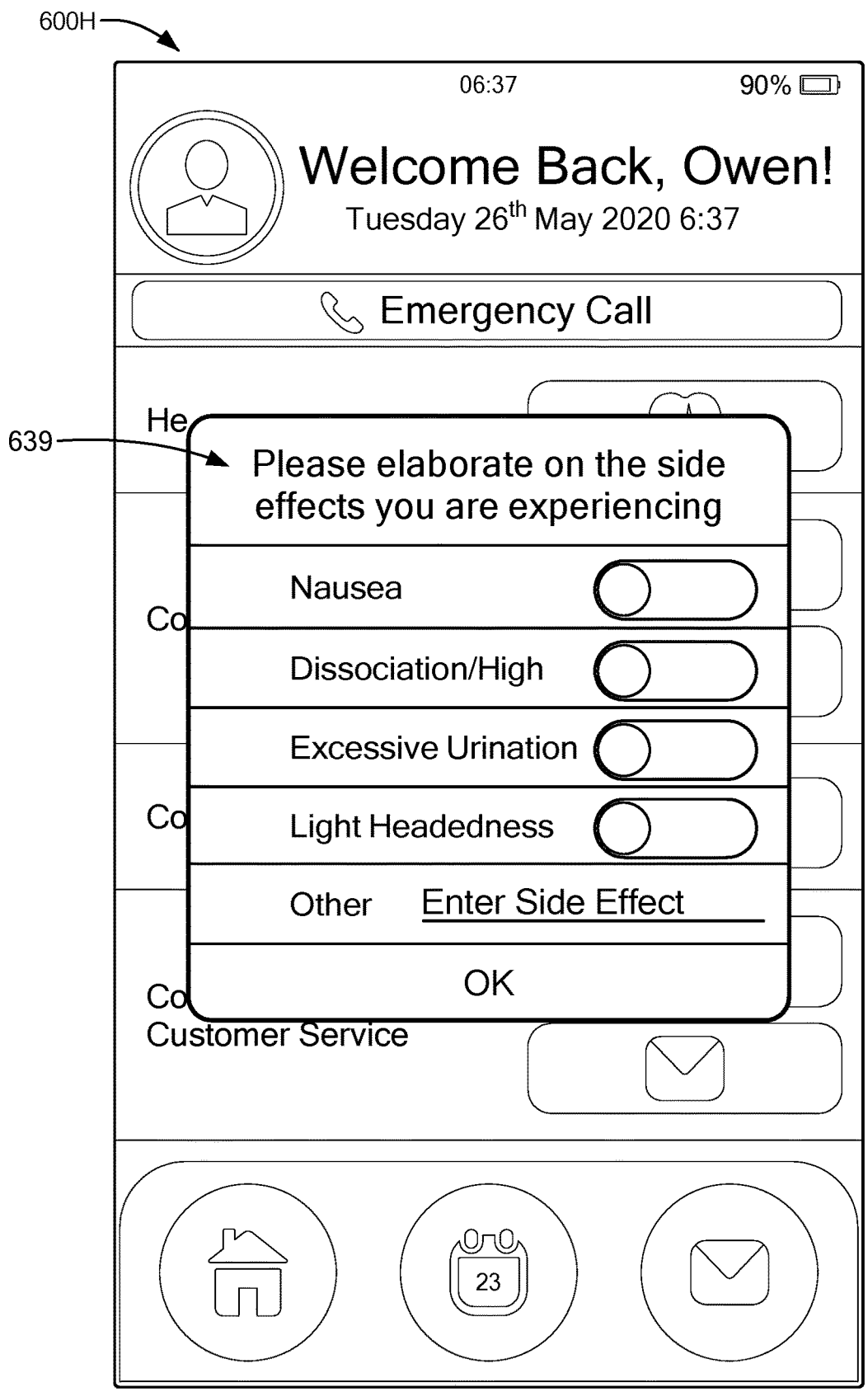

A side-effects display page 600H is presented in FIG. 6H. Display page 600H depicts a side effect inquiry 639 including a request for additional details regarding which side effects the patient is experiencing. Display page 600H receives patient selection of software switches displayed adjacent specific side-effects which may occur when taking the prescribed medication. The likelihood of occurrence, based on clinical trial and post-market reports, may be used to order the potential side-effects. In addition, data entry fields are included in display page 600H to receive patient-entered text providing additional information related to the selected side effects, or to identify side effects not listed as a selectable option.

Figure 7:
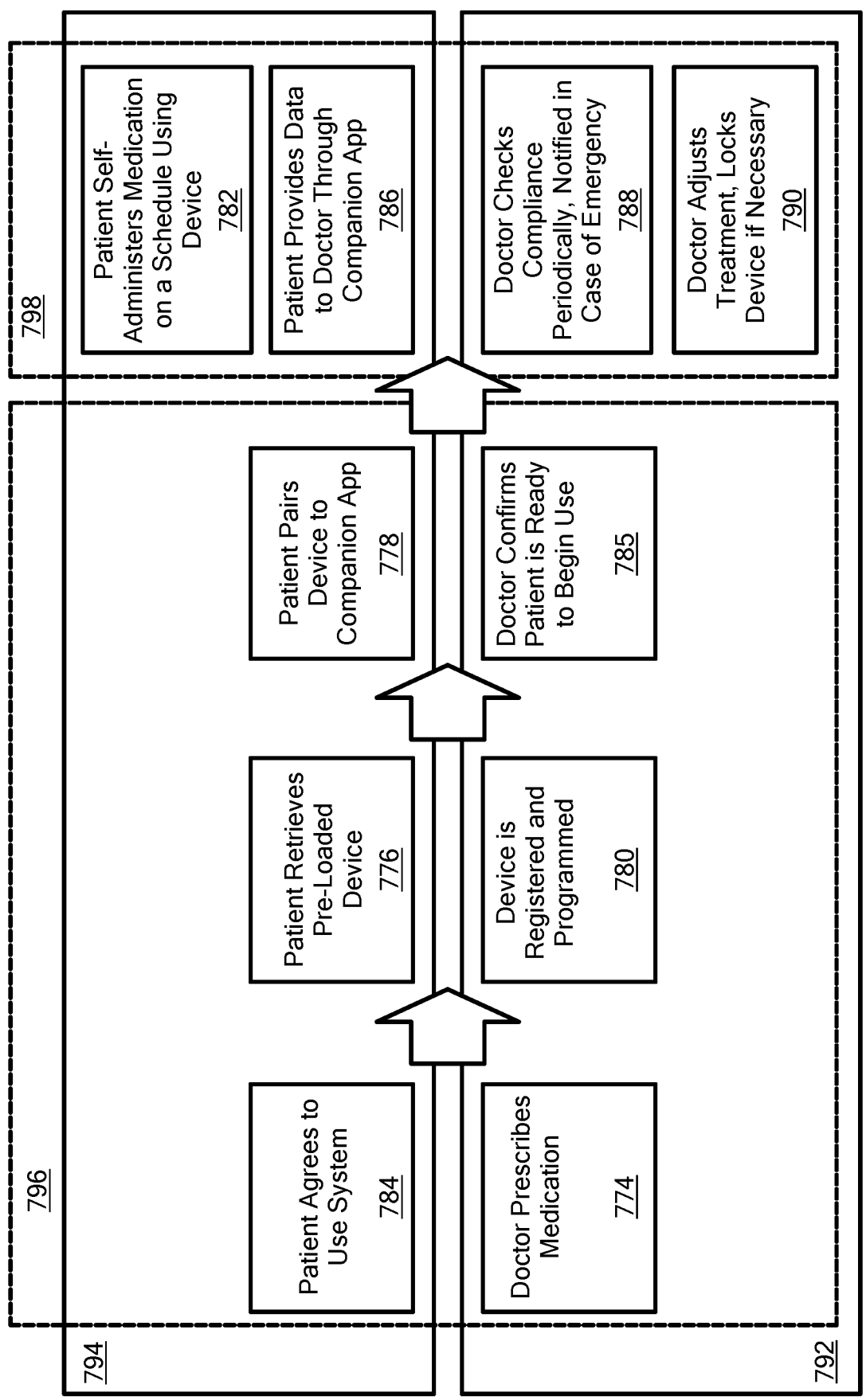
FIG. 7 is a flowchart of an embodiment of a method for the use of a system of the present invention.

FIG. 7 is a flowchart of an embodiment of a method for the use of system 501. Prior to the patient 594 using device 500, a series of steps or functions 796 are performed. After steps 796 are performed, regular use of the system 501 can begin, which entails steps 798. All blocks vertically aligned with each other may occur concurrently. The upper half of FIG. 7, labelled 794, includes those blocks which describe actions performed by patient 594. The lower half of FIG. 7, labelled 792, includes those blocks which describe actions performed by doctor 592.

At block 774, a doctor or other health care provider (HCP) 592 prescribes a medication to the patient. This prescription 574 includes the medication, patient-specific dosage and schedule information, concentration (if the medication is to be compounded) and/or other prescription parameters. The same or different prescription may identify device 500 with the prescribed medication contained therein, Alternatively, device 500 is brought to pharmacy 551 to be filled with the prescribed medication or it may have to be acquired separately. It should be appreciated that a patient may obtain device 500 in a myriad of ways; the prescribed medication on the other hand, is dispensed by pharmacy 551 or other authorized HCP. Distribution of the prescribed medication 576 may be be conditioned on the patient taking particular actions which may include but are not limited to use of system 501, acquisition of the device 500, installation of a companion application 573 on the patient's smartphone or other computing device 568, and acquire any additional external devices 572a deemed necessary by HCP 592.

At block 784, the patient agrees to use system 501 and device 500 and undergo any necessary prerequisite training. The doctor may be the one to recommend or require using system 501, or perhaps the patient, a family member of the patient, or another doctor recommends or requests the use of the system.

At block 776, the patient retrieves a pre-filled device. As noted above, some embodiments of device 500 are disposable while others are refillable. Prefilled device 500 may have been filled by pharmacy 551, the pharmaceutical company manufacturing the prescribed medication, or other authorized entity or individual.

A description of one possible method for filling device 500 with a full Rx dose 576 of a prescribed medication is as follows. Once the doctor transmits prescription 574 to pharmacy 551, the doctor and pharmacist will communicate as needed. It is common practice for doctors to communicate with pharmacists when prescribing compounded medications.

The pharmacist may also ask the doctor's office to unlock the refill hatch 132 of the device 500, which can be done exclusively through the HCP interface 566. The unlocking command 532 is transmitted from the patient management software 561 to the command subassembly 503 on device 500. Other possible embodiments of this process could include a method for the pharmacist to personally input parameters to the system via a pharmacist-specific software or website, and/or unlock the device's refill hatch directly, such as with a manufacturer-issued traditional key or key fob. In other embodiments, the device is disposable and only gets filled once.

One embodiment of system 501 has disposable devices which come pre-filled from the manufacturer. Once the hatch 132 is open, the pharmacist can load in the medication, and when done will close it, at which point the hatch will automatically relock and the device may notify the server that it has been successfully refilled. The return of the loaded device to the patient may be confirmed in the system by the patient via the patient interface. The system could be designed so as to notify all users when it is approaching empty.

At block 780, device 500 is registered and programmed. This programming may include but is not limited to patient identity, dose quantity, dose schedule, and any requirements to be met prior to the patient being able to take dose. These prerequisites to administrations may be values or ranges of values for different parameters selected by the HCP based on the prescribed medication, patient's health, other medications currently being taken, trustworthiness/other risk factors of the patient, or any factor. Exemplary requirements are further described below with reference to FIG. 8.

This programming may be on patient management software 561 or on on-board command subassembly 503. This programming may occur before or after the patient receives device 500. One embodiment of the filling process above requires this programming to be done during the filling process, perhaps by the pharmacist themself, or responsibility could fall on the doctor, pharmacist, manufacturer, or other qualified entity. This programming could occur remotely utilizing software on the server 562, or may require having the physical device 500. In one embodiment of this process 780, the doctor accesses the HCP interface and inputs the patient's device ID into the centralized online system 501. Software assigns a code to the patient's device, retaining all of the patient identification information on server 562.

At block 778, patient establishes access to patient interface 570 on patient's smartphone 568 or equivalent device. The process of obtaining and installing any software may be done with the help of an HCP, or could be a part of the prerequisite training 784 or registering/programming 780. Once 778 is complete, all system 501 users and integrated softwares and devices are paired with one another through server 562, and the patient has an updated entry in the database 564. This process may include downloading a companion app 573 and logging into their patient account.

At block 785, doctor 592 confirms patient 594 is ready to begin treatment using system 501. This confirmation may take place through system 501, over the phone, in person, or through any other method of communication. This confirmation may include ensuring the patient has all necessary devices, software, and training.

At block 782, patient 594 executes patient control actions 553 on device 501 to self-administer a dose 582 of prescribed medication in accordance with dose schedule 547. Step 782 is described in greater detail below in FIG. 8.

At block 786, patient 594 regularly uses patient interface 570. Patient uses patient interface 570 for data collection 586, which may include feedback 523 and input biometric information 537. The patient also may use patient interface 570 for access to information on patient management software 561 on server 562 using Oversight Tools 571.

At block 788, HCP 592 utilizes the monitoring functions of system 501, which may include the review of monitored parameter data 588, by checking compliance periodically through HCP interface 566, receiving notifications in case of emergency, and direct communication with the patient 594.

At block 790, HCP 592 utilizes the regulating functions of system 501, which may include the initiation of control commands 590, by adjusting treatment or shutting down device 500 if necessary through HCP interface 566.

Figure 8:
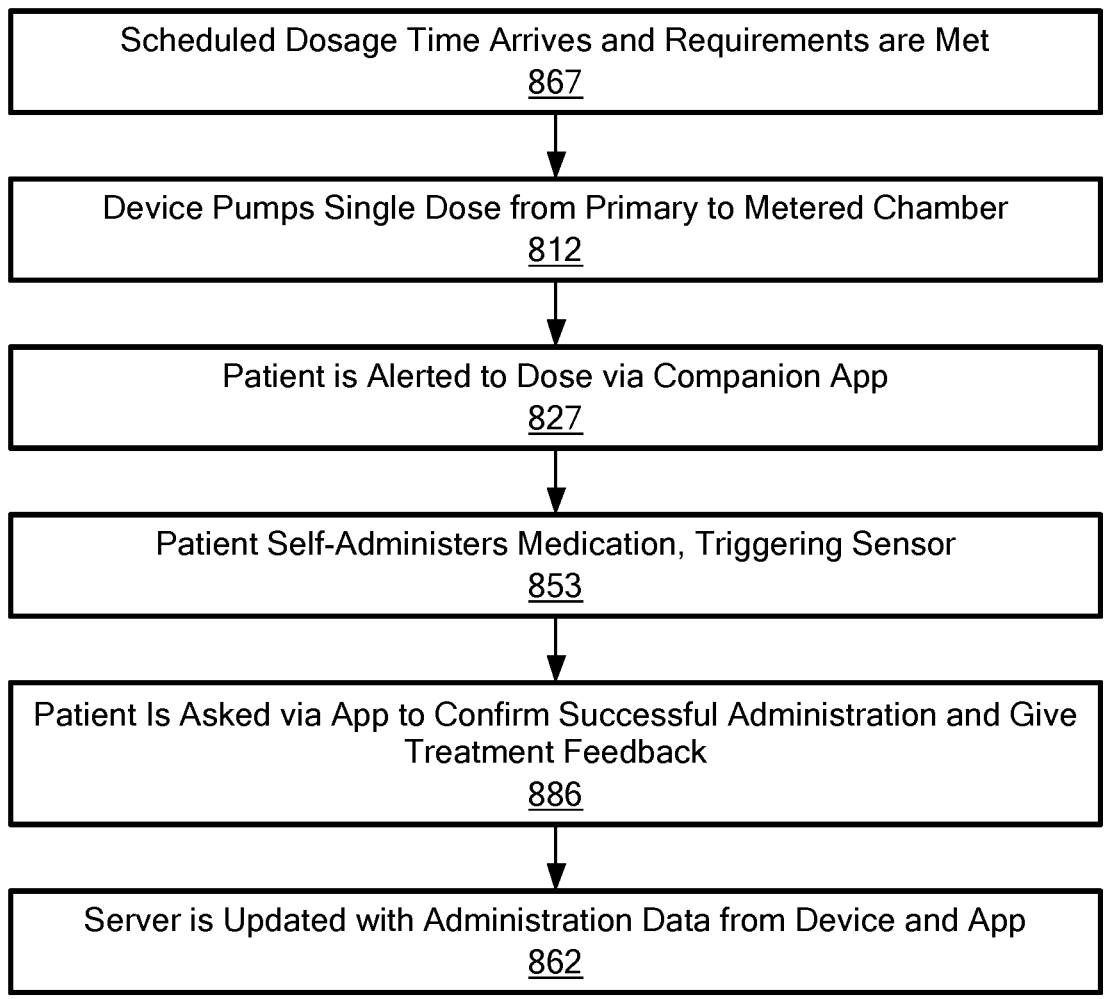
FIG. 8 is a flowchart of an embodiment of a method for the self-administration of a dose of medication using a device of the present invention.

FIG. 8 describes in detail one embodiment of process 782 of self-administering a dose of medication.

At block 867, when a scheduled time arrives at which a dose should be administered, the command subassembly 503 or patient management software 561 on server 562 first confirms that current data from any required accompanying devices is within an approved range. That is, before administration of a dose can be made possible, certain parameters, specified by the doctor upon prescription, must be satisfied. These requirements may include, for example, the patient having a certain health status verifiable by biometric data, the patient inputting certain data into the interface 570, signing an agreement saying they won't operate heavy machinery for a certain period of time after self-administering the medication, confirming that the user is ready and able, confirming the user's identity with a fingerprint scanner or camera, or any other requirement deemed necessary by the HCP.

Certain other parameters that must be met may include but are not limited to: completely successful administrations up to present, enough estimated volume available for dose, lack of a detected tamper event, adequate device battery charge, adequate wireless signal connectivity between device 500 and World Wide Web 559, and successful server 562 connectivity with patient terminal 568. Such biometric data may be input manually by the patient or may be obtained directly from a smart device 572*a*. Such devices may measure heart rate, blood pressure, blood glucose level, etc. If such data is not immediately available, the server prompts the patient via smartphone to make the data available by, for example, blowing into a breathalyzer.

At block 812, once the parameters are confirmed to be successfully met, the patient management software 561 on server 562 will command the device 500 to make a dose available to the patient for self-administration. For device 100, this would include the pumping of one dose from the primary chamber 108 to the metered chamber 110.

At block 827, the patient 594 is alerted to the availability of a dose. This could occur through the patient interface 570 using a popup like 627, or through any other method, such as an automated phone call, text, or email, or device 500 alerts the patient with a noise or LED indicator.

In block 853 the patient self-administers a dose 582 of the prescribed medication, possibly in multiple increments 583. The patient controls delivery interface 504 though application of patient control actions 553. In the nasal spray embodiment of FIG. 2 described above, patient control actions 553 include the manual depression of spray nozzle depressor 238. The administration of the prescribed medication is confirmed by activation of the administration sensor. Alternatively or additionally, such a confirmation may be obtained by monitored subassembly 522 based on detected fluid levels in regulated subassembly 506. The device records the timestamp of dose administration, which is sent to patient management software 561 executing on server 562, which will store the device's timestamped administration confirmation along with the health parameters recorded before dose partitioning. This information is stored in patient database 564 for subsequent presentation to the doctor.

In block 886, after administration has been detected in block 853, the patient is prompted, via patient interface 570, to confirm successful administration and enter into patient interface 570 treatment feedback, utilizing the data collection function of the user interface 586, possibly including input biometrics 537 and/or feedback 523. This step may be performed through an interface state possibly resembling Health Checkup Form 623 and side-effect form 639. This would also be the time at which a patient 594 can report an error in administration, possibly through a button such as 631 or through contact page 600D.

In block 862, server 562, and database 564, are updated with data concerning the particular administration event from device 500, patient interface 570, and any external devices 572*a*. This is likely not to be its own step in the process, and rather would likely happen throughout the self-administration process steps described here in FIG. 8. This is due to the fact that some data is required by the patient management software 561 prior to administration, per prerequisites discussed in block 867, and the patient management software 561 is made aware of an administration event in real-time as discussed in block 853, as to prompt block 886. The data is processed through patient management software 561 on server 562 and logged into database 564. Software 561 may calculate the remaining amount of medication in device 500. If the dose could not be partitioned because one of any of the above parameters were not met, or an error was reported during administration, the device will also record which parameters were not met and store this in the database 564, while notifying the doctor 592 that a dose could not be taken and why. The patient interface 570 and HCP interface 566 are both updated to reflect this data, which may include, for example, the resetting of the countdown timer 609.

Some embodiments of device 500 have a removable primary chamber 108 or a removable cartridge 308, where either pharmacy 551 or HCP 592 is responsible for replacing when the medication is depleted, which in the case of a primary chamber may be after the administration of numerous doses, and after every dose in the case of cartridges.

While some embodiments of the regulated subassembly 506 of device 500 include a dedicated medication transfer mechanism, such as pump 212 and extractor mechanism 312, others may restrict access to a single dose of medication through methods which do not entail the physical transfer of medication. For example some embodiments of regulated subassembly 506 include a single chamber for medication accessible to the delivery interface 504 while restricting how much and at what times patient control actions 553 can be performed. One such embodiment includes a mechanism which locks and unlocks the nasal spray depressor, allowing it to be depressed only a specified number of times (the sum of such applications constituting the administration of a single prescribed dose) and on a specified schedule. Other such embodiments may limit patient control actions 553 based upon data from a fluid flow sensor, fluid volume sensor, or any other sensor which may indicate when one dose has been administered.

In some embodiments of device 100 and 200, both reservoirs are part of a single assembly that is one of a set of such assemblies that are specifically configured for approved dosages and refill durations. For example, one assembly will have a secondary reservoir with a capacity for a first prescribed daily dosage of a particular medication and a primary reservoir with a capacity for a 30 day supply of that dosage of the medication. A second assembly of the set could have reservoirs with a capacity that is 50% greater than the capacity of the corresponding reservoirs in the first assembly to accommodate a second prescribed daily dosage that is 50% more than the first prescribed daily dosage.

In some embodiments of system 501, external device 572a may be implanted or injected into the body of the patient, possibly for the detection of medication concentrations or the detection of chemicals which may make administration of the medication dangerous. For example, such a sensor could be used to confirm administration. In another example, such a sensor is used to confirm a lack of illicit substances in the patient's body prior to making a dose available for administration. Alternative embodiments of such a device or sensor may be incorporated into the medication itself, for example a nanobot within an ingestible pill.

In some embodiments of system 501, dosage schedule 547 may not be a set of predetermined times but rather a set of predetermined criteria, which, if met, indicate the arrival of a scheduled dose. For example, should the medication be insulin, device 572a may be a blood glucose monitor, and only when the patient's blood glucose level is measured to be above/below a threshold does device 500 make a dose of insulin available.

It should be appreciated that various embodiments may be formed with one or more of the above-described features. The above aspects and features may be employed in any suitable combination as the present invention is not limited in this respect. It should also be appreciated that the drawings illustrate various components and features which may be incorporated into various embodiments. For simplification, some of the drawings may illustrate more than one optional feature or component. It should also be appreciated that the present invention is not limited to the specific embodiments disclosed in the drawings. It should be recognized that the invention encompasses embodiments which may include only a portion of the components described above and/or illustrated in any of the referenced drawings, and/or may also encompass embodiments combining components illustrated in multiple different drawing figures.

The provisional patent application from which the present application claims the benefit, U.S. Provisional Patent Application 62/859,138, filed Jun. 9, 2019, is hereby incorporated by reference herein in its entirety.

It should be understood that the foregoing description of various embodiments is intended merely to be illustrative thereof and that other embodiments, modifications, and equivalents are within the scope of the invention recited in the claims appended hereto.

What is claimed is:

1. A device for use by a patient to self-administer a prescribed medication comprising:
   a delivery interface, responsive to patient control actions, configured to administer a dose of the medication to the patient;
   a regulated subassembly configured to store a plurality of doses of the medication in at least one patient-inaccessible storage chamber, and for making single dose quantities of the stored medication available to said delivery interface in accordance with a prescribed dose schedule;
   a monitored subassembly having at least one sensor connected to said device to detect device parameters including detected attempts to tamper with the device, and to remotely transmit said detected device parameters; and
   a command subassembly configured to control said regulated subassembly in response to commands generated by a remote health care provider (HCP) and transmitted to said device.

2. The device of claim 1, wherein said HCP-generated commands comprise one or more of:
   a single dose quantity of the medication; and
   a dosing schedule.

3. The device of claim 1, wherein said monitored device parameters further comprise one or more of the set consisting of:
   administration events;
   fluid levels or quantities;
   battery charge;
   access hatch status;
   device operational state;
   device location; and
   network connection status.

4. The device of claim 1, wherein said monitored subassembly is further configured to monitor patient parameters.

5. The device of claim 4, wherein said sensed patient parameters comprise
   patient biometrics.

6. The device of claim 1, wherein said HCP-generated commands comprise one or more of the commands to
   permit access to the device for prescription refills;
   cease operability of the device; and
   prescription parameters.

7. The device of claim 1, wherein said delivery interface is constructed and arranged to deliver said retrieved medication in a prescribed form via a prescribed delivery method.

8. A distributed system for enabling remote oversight and control over the self-administration of medication by a patient, comprising:
   a device for use by a patient to self-administer a prescribed medication comprising a monitored subassembly having at least one sensor connected to said device to detect device parameters including detected attempts to tamper with the device, and to remotely transmit said detected device parameters, and a command subassembly configured to control the device in response to remotely-generated commands received by the device; and
   a patient management software program, executing on a remote server communicably coupled to said device, wherein said patient management software program receives said transmitted detected device parameters, and stores the detected device parameters for subsequent presentation to a health care provider (HCP), and further configured to generate said commands in response to the HCP and to transit said commands to the device.

9. The system of claim 8, wherein said device comprises:
a delivery interface, responsive to patient control actions, configured to administer a dose of the medication to the patient; and
a regulated subassembly configured to store a plurality of doses of the medication in at least one patient-inaccessible storage chamber, and for making single dose quantities of the stored medication available to said delivery interface in accordance with a prescribed dose schedule.

10. The system of claim 8, wherein said server is communicably connected to one or more external devices, and
wherein said patient management software comprises means for processing data received from said one or more external devices.

11. The system of claim 8, wherein a computing platform is accessible to the patient and communicably connected to the server, and further wherein the system comprises:
a patient interface program, executing on the platform, comprising data collection means for receiving information entered by the patient, said information being related to the patient and the patient's use of said device,
wherein said patient interface program is configured to transmit said patient-entered information to said patient management software executing on the server.

12. The system of claim 11, wherein the local platform is a smartphone and wherein the patient interface program is implemented in a downloadable application program executable on the smartphone.

13. The system of claim 11, wherein said patient interface program further comprises:
means for presenting a selection of device usage data to the patient.

14. The system of claim 11, wherein said patient interface program further comprises:
means for tracking patient use of the device, providing tools to assist the patient in timely administering a dose of the medication using said device.

15. The system of claim 11, wherein said information received by said data collection means comprises:
patient medical conditions; and
patient side-effects related to taking the medication.

16. An apparatus for enabling a remote HCP to regulate and monitor the use of a device used by a patient to self-administer a prescribed medication, the device having a delivery interface, responsive to patient control actions, configured to administer a dose of the medication to the patient, and a storage component to store a plurality of doses of the medication, the apparatus comprising:
a regulated subassembly configured to restrict use of the device such that a single dose quantity of medication is made available to patient in accordance with a prescribed dose schedule;
a monitored subassembly having at least one sensor connected to said device to detect device parameters including detected attempts to tamper with the device, and to remotely transmit said detected device parameters; and
a command subassembly configured to control said regulated subassembly in response to commands generated by a remote health care provider (HCP) and transmitted to said device.

17. The apparatus of claim 16, wherein said monitored device parameters further comprise one or more of the set consisting of:
administration events;
fluid levels or quantities;
battery charge;
access hatch status;
device operational state;
device location; and
network connection status.

18. The apparatus of claim 16, wherein said monitored subassembly is further configured to monitor patient parameters, wherein said sensed patient parameters comprise patient biometrics.

19. The apparatus of claim 16, wherein said HCP-generated commands comprise one or more of the commands to
permit access to the device for prescription refills;
cease operability of the device; and
prescription parameters.

20. The apparatus of claim 16, wherein said apparatus is configured to lockingly attach to the device.

* * * * *